(12) United States Patent
Gharib et al.

(10) Patent No.: US 11,957,438 B2
(45) Date of Patent: *Apr. 16, 2024

(54) METHOD AND APPARATUS FOR LEFT VENTRICULAR END DIASTOLIC PRESSURE MEASUREMENT

(71) Applicant: California Institute of Technology, Pasadena, CA (US)

(72) Inventors: Morteza Gharib, Altadena, CA (US); Niema M. Pahlevan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/452,227

(22) Filed: Aug. 18, 2023

(65) Prior Publication Data
US 2023/0389805 A1 Dec. 7, 2023

Related U.S. Application Data

(63) Continuation of application No. 16/896,976, filed on Jun. 9, 2020, now Pat. No. 11,730,376, which is a
(Continued)

(51) Int. Cl.
*A61B 5/02* (2006.01)
*A61B 5/00* (2006.01)
(Continued)

(52) U.S. Cl.
CPC ........ *A61B 5/02028* (2013.01); *A61B 5/0006* (2013.01); *A61B 5/021* (2013.01);
(Continued)

(58) Field of Classification Search
CPC ... A61B 5/02028; A61B 5/0006; A61B 5/021; A61B 5/0285; A61B 5/318; A61B 7/00
See application file for complete search history.

(56) References Cited

U.S. PATENT DOCUMENTS

| 5,199,438 A | 4/1993 | Pearlman |
| 9,026,193 B2 | 5/2015 | Pahlevan et al. |
| (Continued) | | |

FOREIGN PATENT DOCUMENTS

WO  WO 2019/144058  7/2019

OTHER PUBLICATIONS

Garrard, JR., C.L., et al., *The Relationship of Alterations in Systolic Time Intervals to Ejection Fraction in Patients with Cardiac Disease*, Circulation 42(3): 455-62 (Sep. 1970).
(Continued)

*Primary Examiner* — Paula J Stice
(74) *Attorney, Agent, or Firm* — Knobbe Martens Olson & Bear, LLP

(57) ABSTRACT

A non-invasive and convenient method and apparatus for approximation of left ventricular end diastolic pressure (LVEDP) can be used in both hospital/clinic environments and nursing home or home environments. The method and apparatus use non-invasive sensors and a new "cardiac triangle" computational method to obtain an approximation of LVEDP. The computational method uses hemodynamic and electrocardiogram (ECG) waveforms as input, which can be collected by a portable device or devices.

28 Claims, 15 Drawing Sheets

Related U.S. Application Data continuation of application No. PCT/US2019/014378, filed on Jan. 18, 2019.

(60) Provisional application No. 62/623,095, filed on Jan. 29, 2018, provisional application No. 62/618,988, filed on Jan. 18, 2018.

(51) Int. Cl.
- *A61B 5/021* (2006.01)
- *A61B 5/022* (2006.01)
- *A61B 5/0285* (2006.01)
- *A61B 5/318* (2021.01)
- *A61B 7/00* (2006.01)

(52) U.S. Cl.
CPC ........ *A61B 5/02233* (2013.01); *A61B 5/0285* (2013.01); *A61B 5/318* (2021.01); *A61B 7/00* (2013.01)

(56) References Cited

U.S. PATENT DOCUMENTS

| | | |
|---|---|---|
| 11,730,376 B2 | 8/2023 | Gharib et al. |
| 2004/0220637 A1* | 11/2004 | Zdeblick ............ A61B 5/14539 607/17 |
| 2004/0254483 A1 | 12/2004 | Zdeblick et al. |
| 2006/0235309 A1 | 10/2006 | McIntyre |
| 2009/0030292 A1 | 1/2009 | Bartnik et al. |
| 2009/0112113 A1 | 4/2009 | Mukkamala |
| 2012/0179382 A1* | 7/2012 | Zhang ................. A61B 5/7264 702/19 |
| 2015/0265163 A1* | 9/2015 | Marmor .................. A61B 7/00 600/493 |
| 2017/0020414 A1 | 1/2017 | Zdeblick et al. |

OTHER PUBLICATIONS

Lewis BS, et al., *Predictive value of the systolic time intervals in primary myocardial disease*, Chest 64(4): 431-38 (Oct. 1973).

Lewis RP, et al., *A Critical Review of the Systolic Time Intervals*, Circulation 56(2): 146-58 (Aug. 1977).

Newlin DB, et al., *Pre-ejection Period: Measuring Beta-adrenergic Influences Upon the Heart*, Psychophysiology 16(6): 546-552 (Nov. 1979).

* cited by examiner

FIG. 2D
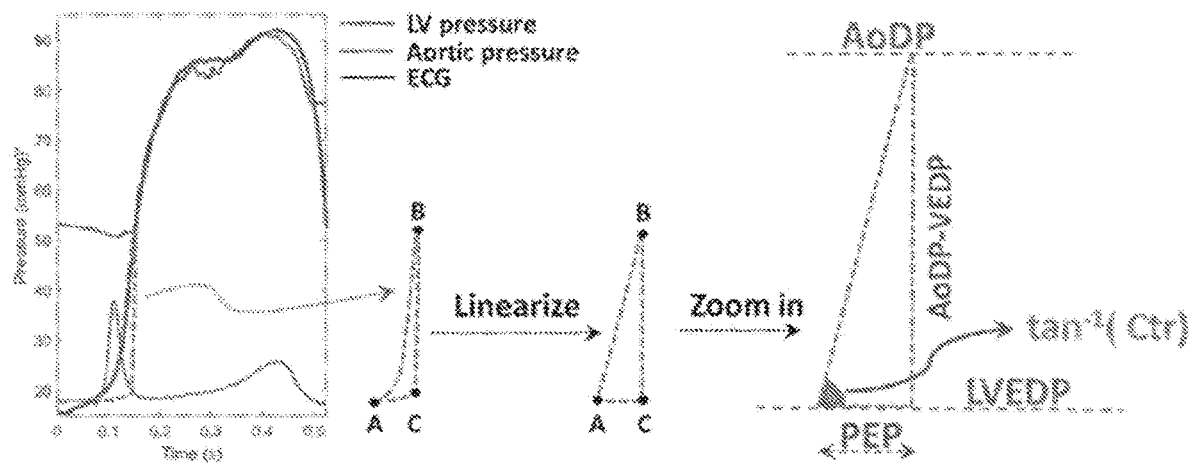
FIG. 2E
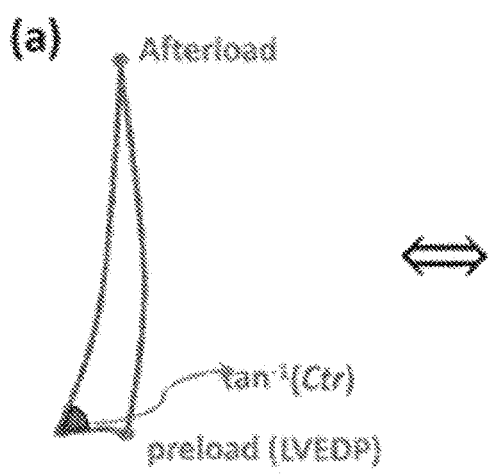
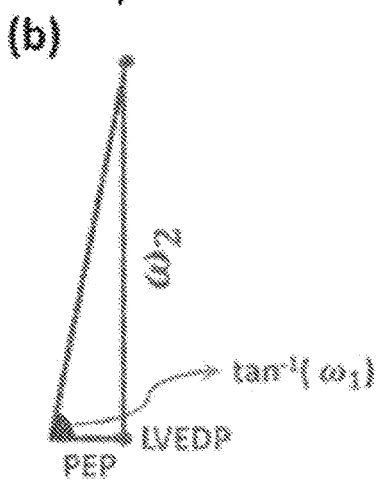

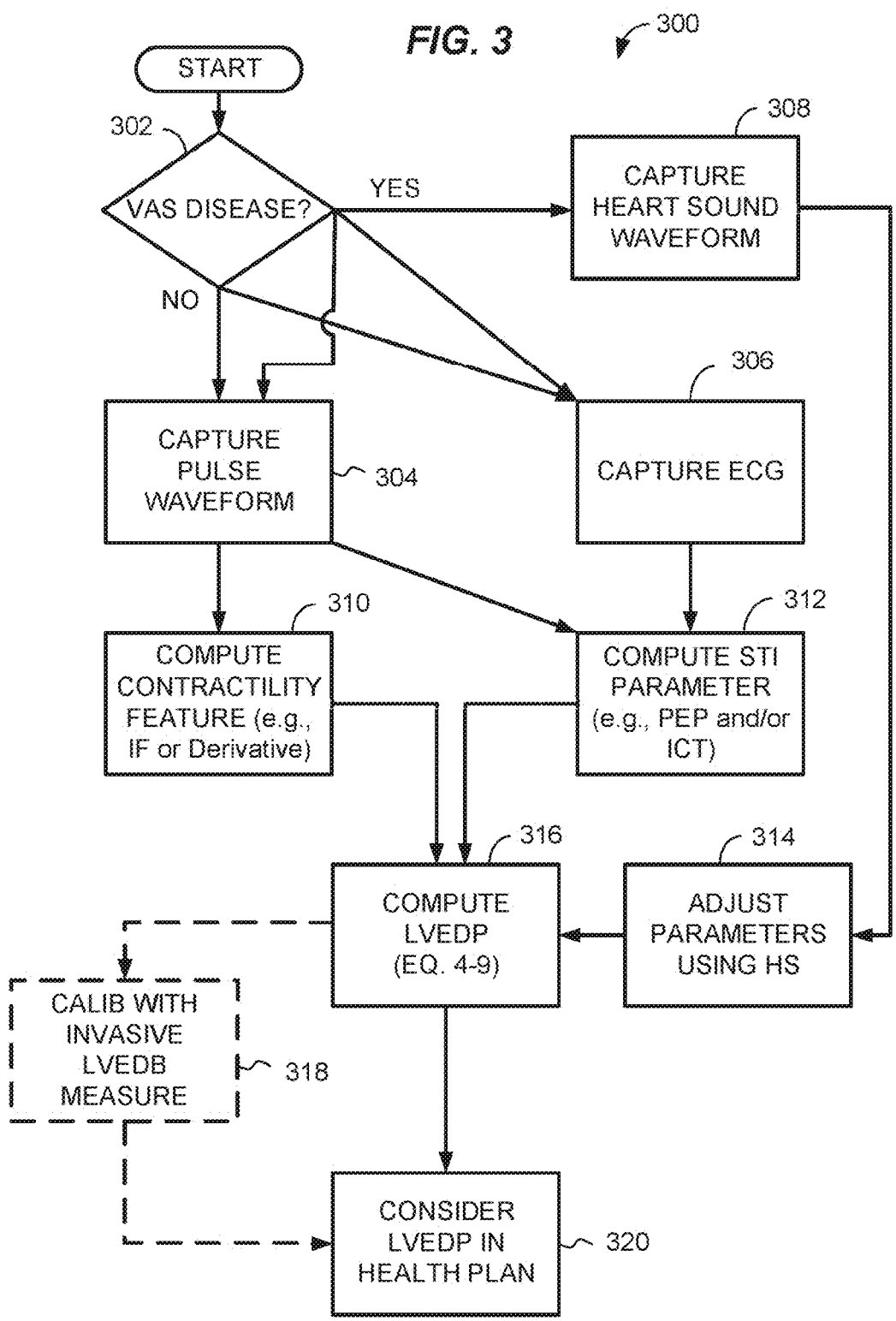

510 — RECEIVING, BY AT LEAST ONE PROCESSOR, HEMODYNAMIC WAVEFORM DATA FROM A NON-INVASIVE SENSOR COUPLED TO A PATIENT

520 — RECEIVING, BY THE AT LEAST ONE PROCESSOR, ELECTROCARDIOGRAM (ECG) DATA OR HEART SOUND WAVEFORM DATA FROM A SECOND NON-INVASIVE SENSOR COUPLED TO THE PATIENT

530 — DETERMINING, BY THE AT LEAST ONE PROCESSOR, AT LEAST ONE OF A PRE-EJECTION PERIOD (PEP) OR AN ISOVOLUMIC CONTRACTION TIME (ICT), BASED ON SIMULTANEOUS PORTIONS OF THE HEMODYNAMIC WAVEFORM DATA AND AT LEAST ONE OF THE ECG DATA OR THE HEART SOUND WAVEFORM DATA

540 — CALCULATING, BY THE AT LEAST ONE PROCESSOR, AN LVEDP BASED ON A CONTRACTILITY FEATURE AND AT LEAST ONE OF THE PEP AND ICT

550 — ENCODING THE LVEDP AS DIGITAL DATA FOR AT LEAST ONE OF STORAGE, TRANSMISSION, OR HUMAN-COMPREHENSIBLE OUTPUT

780
CALCULATING, BY THE AT LEAST ONE PROCESSOR A CONTRACTILITY FEATURE BASED ON THE HEMODYNAMIC WAVEFORM DATA

790
THE AT LEAST ONE PROCESSOR CALCULATES THE LVEDP AS A FUNCTION OF THE INTRINSIC FREQUENCIES, THE PEP, AND A CUFF BLOOD PRESSURE (DBP)

1260
CALCULATING THE TIME FEATURES AND WAVEFORM FEATURES OF THE HWD AND THE AT LEAST ONE OF ECG DATA OR HSW DATA BASED ON AT LEAST ONE OF: CAROTID PRESSURE WAVEFORM, AORTIC WALL WAVEFORM, CAROTID VESSEL WALL WAVEFORM, RADIAL PRESSURE WAVEFORM, RADIAL VESSEL WALL WAVEFORM, BRACHIAL PRESSURE WAVEFORM, BRACHIAL VESSEL WALL WAVEFORM, FEMORAL PRESSURE WAVEFORM, FEMORAL VESSEL WALL WAVEFORM, OR PULSEOX WAVEFORM

1270
CALCULATING THE TIME FEATURES AND WAVEFORM FEATURES OF THE HWD AND THE AT LEAST ONE OF ECG DATA OR HSW DATA BASED ON OR SUPPLEMENTED WITH AT LEAST ONE OF: CALCULATING A SURROGATE FROM NON-INVASIVELY MEASURED EF OR FS

1280
CALCULATING THE TIME FEATURES AND WAVEFORM FEATURES OF THE HWD AND THE AT LEAST ONE OF ECG DATA OR HSW DATA BASED ON OR SUPPLEMENTED WITH AT LEAST ONE OF A FLOW OR VELOCITY WAVEFORM

810
DETERMINING, BY THE AT LEAST ONE PROCESSOR, A PULSE WAVE VELOCITY FROM THE HEMODYNAMIC WAVEFORM DATA

820
CALCULATING THE AT LEAST ONE OF THE PEP AND THE ICT USING THE PULSE WAVE VELOCITY TO IMPROVE ACCURACY

910
CALCULATING THE CONTRACTILITY FEATURE IS BASED ON AT LEAST ONE OF: CAROTID PRESSURE WAVEFORM, AORTIC WALL WAVEFORM, CAROTID VESSEL WALL WAVEFORM, RADIAL PRESSURE WAVEFORM, RADIAL VESSEL WALL WAVEFORM, BRACHIAL PRESSURE WAVEFORM, BRACHIAL VESSEL WALL WAVEFORM, FEMORAL PRESSURE WAVEFORM, FEMORAL VESSEL WALL WAVEFORM, OR PULSOX WAVEFORM

920
CALCULATING THE CONTRACTILITY FEATURE IS BASED ON AT LEAST ONE OF: CALCULATING A SURROGATE FROM NON-INVASIVELY MEASURED EJECTION FRACTION (EF) AND FRACTIONAL SHORTENING (FS)

920
CALCULATING THE CONTRACTILITY FEATURE IS BASED ON AT LEAST ONE OF A FLOW OR VELOCITY WAVEFORM

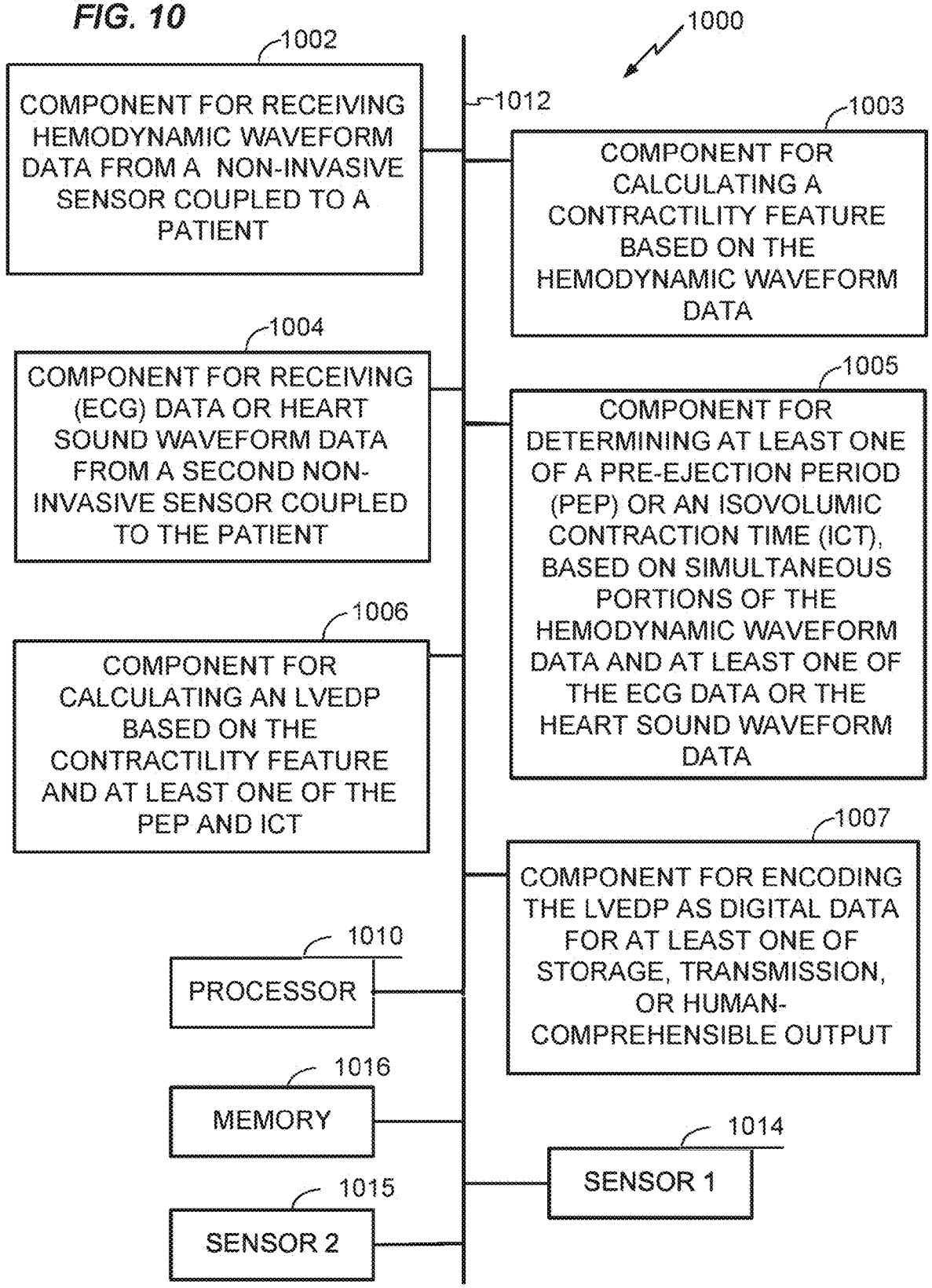

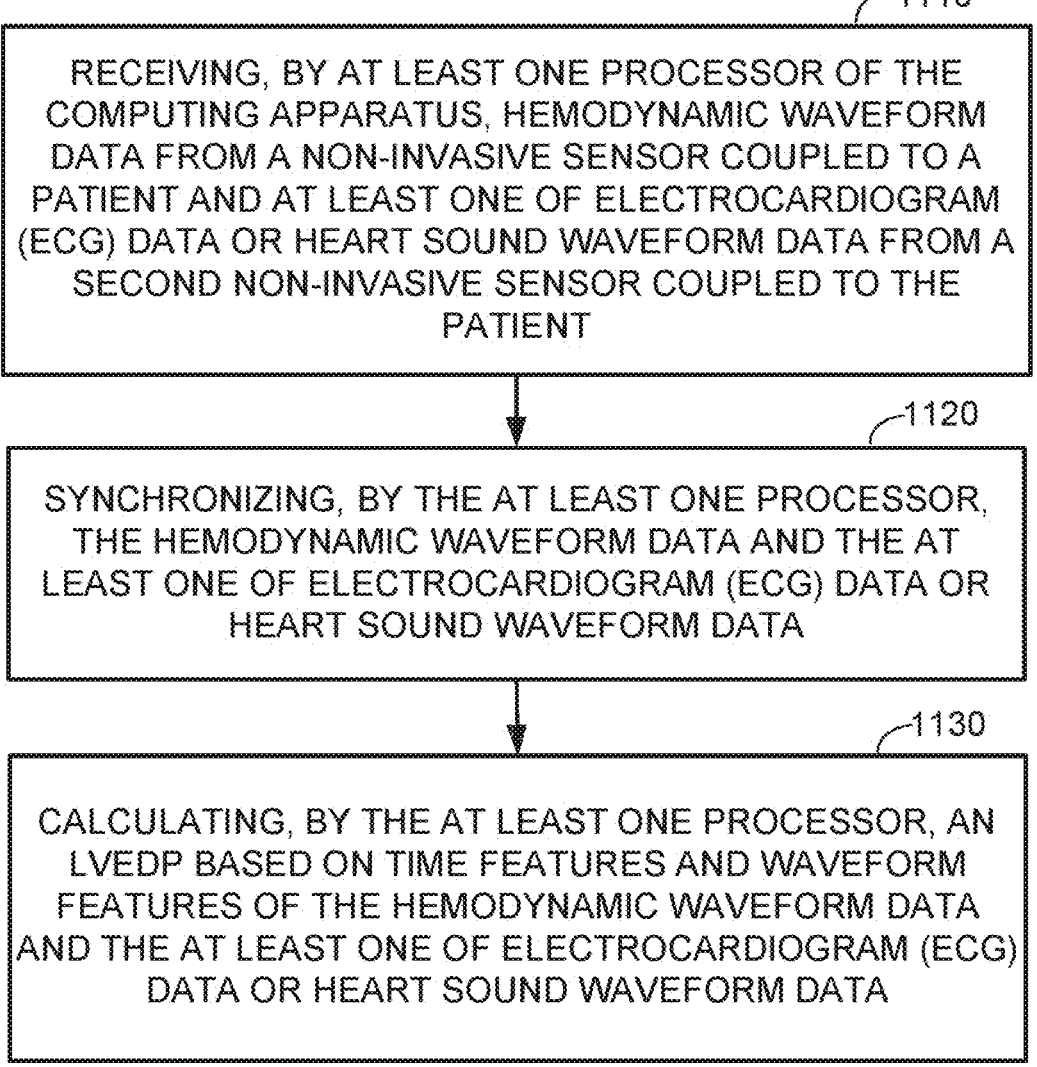

┌─ 1210
ENCODING THE LVEDP AS DIGITAL DATA FOR AT LEAST ONE OF STORAGE, TRANSMISSION, OR HUMAN-COMPREHENSIBLE OUTPUT

┌─ 1220
DETERMINING, BY THE AT LEAST ONE PROCESSOR, AT LEAST ONE OF A PRE-EJECTION PERIOD (PEP) OR AN ISOVOLUMIC CONTRACTION TIME (ICT), BASED ON SIMULTANEOUS PORTIONS OF THE HEMODYNAMIC WAVEFORM DATA AND AT LEAST ONE OF THE ECG DATA OR THE HEART SOUND WAVEFORM DATA

┌─ 1230
CALCULATING, BY THE AT LEAST ONE PROCESSOR, A CONTRACTILITY FEATURE BASED ON THE HEMODYNAMIC WAVEFORM DATA

┌─ 1240
THE CONTRACTILITY FEATURE COMPRISES AT LEAST ONE OF A DERIVATIVE OF THE HEMODYNAMIC WAVEFORM DATA OR INTRINSIC FREQUENCIES

┌─ 1250
CALCULATING THE LVEDP AS A FUNCTION OF THE CONTRACTILITY FEATURE, AT LEAST ONE OF THE PEP AND THE ICT, AND OPTIONALLY A CUFF BLOOD PRESSURE (DBP)

METHOD AND APPARATUS FOR LEFT VENTRICULAR END DIASTOLIC PRESSURE MEASUREMENT

PRIORITY CLAIM

The present application is a continuation of U.S. application Ser. No. 16/896,976, filed Jun. 9, 2020, now U.S. Pat. No. 11,730,376, which is a continuation of International Application No. PCT/US19/14378, filed Jan. 18, 2019, which claims priority to U.S. Provisional No. 62/623,095, filed Jan. 29, 2018, and U.S. Provisional No. 62/618,988, filed Jan. 18, 2018, all of which are incorporated by reference in their entireties.

FIELD

The present application relates to methods and apparatus for measurement of left ventricular end diastolic pressure (LVEDP).

BACKGROUND

Heart failure (HF) is a condition in which the heart fails to pump enough blood to meet the body's metabolic demands. Current estimate shows that approximately 5.7 M adults suffer from HF in United States, and this number is expected to increase to 8 M within the next 15 years.

Left ventricular end diastolic pressure (LVEDP) is an important measure of left ventricle function. Elevated LVEDP is generally indicative of poor left ventricular (LV) function in patients experiencing heart failure with preserved ejection fraction (HFpEF) or heart failure with reduced ejection fraction (HFrEF). Therefore, LVEDP is a useful index in management of HF and evaluating the risk of cardiac complications after myocardial infarction (AMI).

Direct measurement of LVEDP includes a highly invasive procedure when it is measured during routine angiography catheterization in CathLab. Indirect evaluation of LVEDP that is being used in critical care units is based pulmonary capillary wedge pressure (PCWP) or pulmonary artery diastolic pressure (PADP) measurement utilizing inflated balloon catheters. These indirect methods are invasive and can only be used in hospital environment. Additionally, these indirect methods are inaccurate in disease conditions such as mitral valve disease and pulmonary vascular diseases. For example, indirect methods overestimate LVEDP in mitral stenosis.

Efforts have been made to approximate LVEDP noninvasively. Most of these methods are based on bulky imaging modalities such Echocardiogram. Other investigators have introduced non-invasive methods of approximating LVEDP without imaging modalities. However, these methods are either hybrid (need some invasive measurement) or they require simultaneous arterial pressure and expiratory pressure during Valsalva maneuver. Therefore, current methods for non-invasive approximation of LVEDP, like invasive measurements of LVEDP, can only be employed in a hospitals or clinic environments.

It would be desirable, therefore, to develop new methods and other new technologies for non-invasive approximation of LVEDP, that overcomes these and other limitations of the prior art.

SUMMARY

This summary and the following detailed description should be interpreted as complementary parts of an integrated disclosure, which parts may include redundant subject matter and/or supplemental subject matter. An omission in either section does not indicate priority or relative importance of any element described in the integrated application. Differences between the sections may include supplemental disclosures of alternative embodiments, additional details, or alternative descriptions of identical embodiments using different terminology, as should be apparent from the respective disclosures.

In present disclosure describes a novel non-invasive and easy-to-use method and apparatus for approximation of LVEDP that can be used in both hospital/clinic environment and at nursing home or home environment. The method and apparatus do not need any physiologic or pharmacologic maneuvers such as the Valsalva maneuver. Instead, the method is based on a non-invasive arterial waveform measurement and electrocardiogram (ECG), both of which can be done by a simple portable device or devices. The method can also be done as a part of a routine cardiac MM procedure. IN addition, the methods as described herein may be adapted for semi-invasive and beat-to-beat evaluation of LVEDP with inline radial cath pressure measurement in hospital or clinic environments.

In an aspect of the disclosure, method for approximation of left ventricular end diastolic pressure (LVEDP) using non-invasive sensors coupled to a computing apparatus may include receiving, by at least one processor of the computing apparatus, hemodynamic waveform data from a non-invasive sensor coupled to a patient. The method may further include receiving, by the at least one processor, electrocardiogram (ECG) data or heart sound waveform data from a second non-invasive sensor coupled to the patient. The method may further include determining, by the at least one processor, at least one of a pre-ejection period (PEP) or an isovolumic contraction time (ICT), based on simultaneous portions of the hemodynamic waveform data and at least one of the ECG data or the heart sound waveform data. The method may further include calculating, by the at least one processor, an LVEDP based on the intrinsic frequencies and at least one of the PEP and the ICT. The method may further include encoding the LVEDP as digital data for at least one of storage, transmission, or human-comprehensible output.

In some embodiments, the method may further include calculating, by the at least one processor, a contractility feature, for example intrinsic frequencies or a derivative of a waveform, based on the hemodynamic waveform data. In related, alternative aspects of the method, the at least one processor may calculate the LVEDP as a function of the contractility feature and the PEP; as a function of the contractility feature, the PEP, and a cuff blood pressure (DBP); as a function of the contractility feature and the ICT; as a function of the contractility feature, the ICT, and a cuff blood pressure (DBP); as a function of the contractility feature, the PEP, and the ICT; and/or as a function of the contractility feature, the PEP, the ICT, and a cuff blood pressure (DBP).

In some embodiments, the method may include collecting a heart sound waveform. In such cases, the method may further include correcting the calculating of the LVEDP for valvular diseases based on the heart sound waveform.

In some embodiments, the method may include determining a pulse wave velocity from the hemodynamic waveform data. The method may further include calculating the at least one of the PEP and the ICT using the pulse wave velocity to improve accuracy.

In an aspect of the method, calculating the intrinsic frequencies may be based on at least one of: carotid pressure waveform, aortic wall waveform, carotid vessel wall waveform, radial pressure waveform, radial vessel wall waveform, brachial pressure waveform, brachial vessel wall waveform, femoral pressure waveform, femoral vessel wall waveform, or pulsOx waveform. Calculating the intrinsic frequencies may be based on at least one of: calculating a surrogate from non-invasively measured ejection fraction (EF) and fractional shortening (FS). Calculating the intrinsic frequencies is based on at least one of a flow or velocity waveform.

As used herein, a "client device" or LVEDP apparatus includes at least a computer processor coupled to a memory and to one or more ports, including at least one input port and at least one output port (e.g., a desktop computer, laptop computer, tablet computer, smartphone, PDA, etc.). A computer processor may include, for example, a microprocessor, microcontroller, system on a chip, or other processing circuit. As used herein, a "processor" means a computer processor. An LVEDP apparatus or client device includes a memory coupled to at least one processor, the memory holding instructions that when executed by the processor cause the apparatus or client device to perform operations of the methods described herein. An LVEDP apparatus or client device may further include non-invasive sensors for capturing a patient's hemodynamic, ECG, and/or heart sound waveforms.

To the accomplishment of the foregoing and related ends, one or more examples comprise the features hereinafter fully described and particularly pointed out in the claims. The following description and the annexed drawings set forth in detail certain illustrative aspects and are indicative of but a few of the various ways in which the principles of the examples may be employed. Other advantages and novel features will become apparent from the following detailed description when considered in conjunction with the drawings and the disclosed examples, which encompass all such aspects and their equivalents.

BRIEF DESCRIPTION OF THE DRAWINGS

The features, nature, and advantages of the present disclosure will become more apparent from the detailed description set forth below when taken in conjunction with the drawings in which like reference characters identify like elements correspondingly throughout the specification and drawings.

FIG. 2B-2E are graphs showing further relationships and aspects of the cardiac triangle and related method.

FIG. 3 is a flow chart illustrating aspect of LVEDP approximation for a patient.

FIG. 5 is a flow diagram illustrating aspects of a method for non-invasive approximation of LVEDP for use by an apparatus as shown in FIG. 4 or 10.

FIGS. 6-9 are flow charts illustrating additional aspects for use with the method of FIG. 5.

FIG. 10 is a conceptual block diagram illustrating components of an apparatus or system for non-invasive approximation of LVEDP.

FIG. 11 is a flow diagram illustrating aspects of an alternative method for non-invasive approximation of LVEDP for use by an apparatus as shown in FIG. 4 or 10.

FIGS. 12A-B are flow charts illustrating additional aspects for use with the method of FIG. 11.

DETAILED DESCRIPTION

Various aspects are now described with reference to the drawings. In the following description, for purposes of explanation, numerous specific details are set forth in order to provide a thorough understanding of one or more aspects. It may be evident, however, that the various aspects may be practiced without these specific details. In other instances, well-known structures and devices are shown in block diagram form in order to facilitate describing these aspects.

Operation of the apparatus and methods described herein may be better understood in view of fundamentals of cardiac measurement parameters. Intrinsic frequency (IF) method is a new method for analysis of coupled dynamical systems described by the inventors hereof. In its simplest form a coupled dynamical system is composed of two systems. A physiological example of a coupled dynamical system is left ventricle-aortic system. The IF method reveals clinically useful information when applied to arterial pressure waveform (the output of LV-Aortic system). The intrinsic frequencies of systemic pressure waves are called cardiovascular intrinsic frequencies denoted by $\omega_1$ and $\omega_2$. $\omega_1$ is the intrinsic frequency of the LV mostly dominated by the dynamics of the LV and $\omega_2$ is the intrinsic frequency of the aortic system that is mostly dependent on the dynamics of the aorta and vascular network.

Our previous studies (unpublished) have shown that Wi is mainly determined by the LV contractility (Ctr) while $\omega_2$ is mostly determined by the arterial wave dynamics and afterload. In addition, the difference between $\omega_1$ and $\omega_2$ ($\omega_1-\omega_2$) can be a measure of LV-arterial coupling (LVAC).

Pre-ejection period (PEP) is one of the systolic time interval (STI) parameters that is mainly dependent on the dynamics of the heart. Past studies showed that PEP is influenced by LV contractility (Ctr), left ventricle end diastolic pressure (LVEDP), and afterload (AL).

Although STI method is an obsolete method of practice in cardiology and has been abandoned since the early 80s, one of its parameters, PEP, can add considerable value to IF method. Mathematically, PEP is orthogonal to $\omega_1$ and $\omega_2$, and other IF dimensions. This means that PEP provides information that cannot be retrieved from IF five-dimensional (5D) space. One of the critically important parameters that can be computed by the combination of PEP and IFs is LVEDP.

Figure 1:
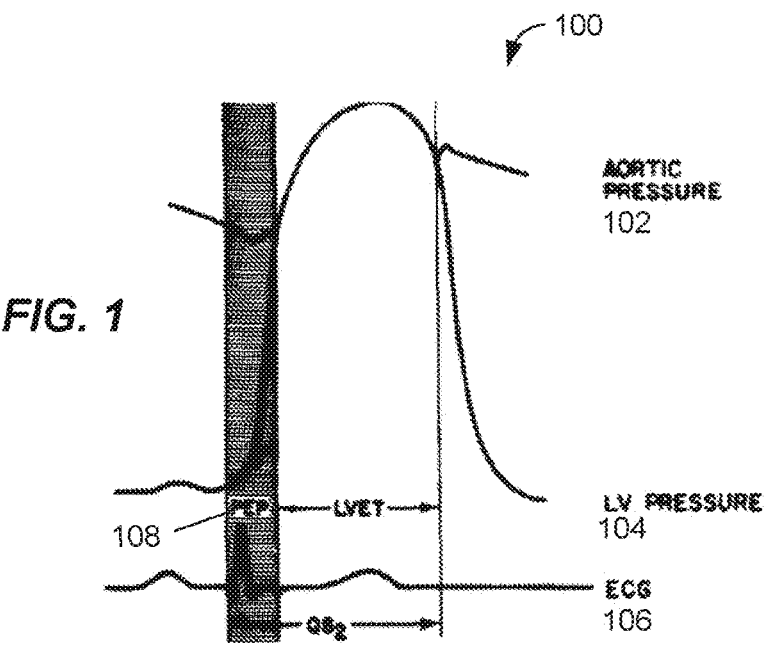
FIG. 1 is a chart illustrating fundamental properties of hemodynamic waveforms as known in the art.

FIG. 1, adopted from Lewis, Richard P., et al. Circulation 56.2 (1977): 146-158), shows a graph 100 of arterial (aortic) pressure waveform 102, left ventricular (LV) pressure 104, ECG 106, and pre-ejection period (PEP) 108 during a cardiac cycle. All the illustrated parameters may be measured non-invasively using new or prior art methods.

Figure 2A:
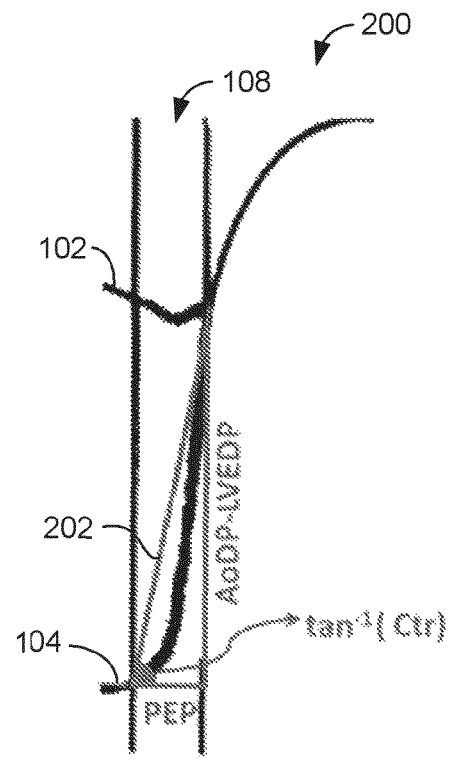
FIG. 2A is a detail of the chart shown in FIG. 1, illustrating relationships between fundamental properties as a "cardiac triangle."

The measurement parameters of a cardiac shown in graph 100 can be used to compute LVEDP using a "cardiac triangle," so called because of a triangular relation between involved parameters. FIG. 2 illustrates computation of LVEDP using a cardiac triangle in the PEP 108 shown in FIG. 1, as an example, wherein AoDP is the aortic diastolic pressure, LVEDP is the value of the LV end diastolic pressure, and "Ctr" is the LV contractility. A triangle 202 is defined by the width of the PEP 108 as one side and the difference between LVEDP and AoDP as the other side. The slope of the hypotenuse of the cardiac triangle is a function ($\tan^{-1}$) of LV contractility. The AoDP is the aortic diastolic pressure that is dependent on the systemic vascular tone and LV-arterial coupling. LVEDP may be computed from the Cardiac Triangle, as follows.

Using FIG. 2, the slope of the contractility function Ctr can be written as:

$$Ctr = \frac{AoDP - LVEDP}{PEP} \tag{1}$$

Solve for LVEDP gives:

$$LVEDP = AoDP - Ctr \times PEP \tag{2.0}$$

In a more general form:

$$LVEDP = a_0 + a_1 AoDP + a_2 Ctr \times PEP \tag{3.0}$$

Where, $a_i$ can be universal physiological constant or a patient specific constant.

In a simplest form AoDP can be approximated by a brachial cuff pressure or any other noninvasive techniques for diastolic blood pressure measurement (DBP).

Ctr can be approximated using different methods, including at least following approaches:
1. The derivative of the carotid pressure waveform before the reflected wave arrival time.
2. The maximum positive derivative of the carotid pressure wave before the first local maximum.
3. The ratio of maximum positive derivative of the carotid pressure waveform divided by the slope of the descending part of the carotid pressure waveform after the dicrotic notch or as it described by Newlin et al (Newlin D B, Levenson R W (1979) Pre-ejection Period: Measuring Beta-adrenergic Influences Upon the Heart. Psychophysiology 16: 546-552).
4. The maximum positive derivative of the carotid pressure wave before the first local maximum to the pulse pressure (pulse pressure=arterial systolic pressure–arterial diastolic pressure).
5. The ratio of the derivative of the carotid pressure waveform before the reflected wave arrival time to the pulse pressure.
6. The ratio of the derivative of the carotid pressure waveform before the reflected wave arrival time to the pulse pressure.
7. As an alternative to carotid pressure waveform in 1-6, aortic wall waveform, carotid vessel wall waveform, radial pressure waveform, radial vessel wall waveform, brachial pressure waveform, brachial vessel wall waveform, femoral pressure waveform, femoral vessel wall waveform, or pulseOx waveform can be used.
8. As a different approach the maximum slope before the peak of aortic, carotid, or other large vessels flow waveform can be used to approximate Ctr.

Noninvasively measured ejection fraction (EF) and fractional shortening (FS) from echo, CTScan or MRI can be used as a surrogate of Ctr.

In a general form, AoDP can be replaced with afterload (AL) and LV-arterial coupling (LVAC). Also, the slope can be written as a function of Ctr. More generally:

$$LVEDP = K_1(Ctr, LVAC, AL, PEP) \tag{4.0}$$

Another way of computing LVEDP from Cardiac Triangle is to use isovolumic contraction time (ICT). In this case the, Equation 4.0 and 5.0 can be written as:

$$LVEDP = K_2(Ctr, LVAC, AL, ICT) \tag{5.0}$$

Combination of both ICT and PEP may also be sued to increase the accuracy of the LVEDP approximation:

$$LVEDP = K_3(Ctr, LVAC, AL, ICT, PEP) \tag{6.0}$$

In cases of valvular diseases such as mitral valve and aortic valve diseases, the sound wave can be used to correct for Equations 2.0 through 6.0. The contractility index in Equations 2.0 through 6.0 can be measured from carotid waveform, radial waveform, femoral waveform or pulseOx waveform. Depending on the location waveform measurement the functions ($K_1$-$K_3$) may be different. All of the parameters in Equations 2.0, 3.0 and 4.0 can be measured non-invasively using portable devices. Waveforms measured using non-invasive methods may sometimes be referred to herein as "non-invasive waveforms."

In some embodiments, the computation may make use of intrinsic frequency (IF) parameters as a special case of Ctr, as described in more detail herein below. The IF parameters $\omega_1$ and $\omega_2$ may be computed from non-invasively collected hemodynamic waveforms as described in U.S. Pat. No. 9,026,193 by inventors hereof (the '193 Patent), which is incorporated by reference herein. For example, $\omega_1$ and $\omega_2$ may be computed using the Sparse Time-Frequency Representation (STFR) method, using Equation 2 in the '193 Patent.

AL, LVAC, and Ctr are related to intrinsic frequency parameters $\omega_1$ and $\omega_2$, as follows:

$$f_1(IFs) = \frac{f_2(IFs) - LVEDP}{PEP} \tag{2.1}$$

Solving Equation 2.1 for LVEDP results in:

$$LVEDP = f_2(IFs) - PEP \times f_1(IFs) \tag{3.1}$$

More generally:

$$LVEDP = K_1(IFs, PEP) \tag{4.1}$$

Thus, LVEDP can be computed from IF parameters and PEP, all of which can be collected non-invasively.

In an aspect, since brachial diastolic pressure is almost the same as AoDP, including cuff blood pressure (DBP) may increase the accuracy of the Equation 4.1:

$$LVEDP = K_2(IFs, PEP, DBP) \tag{5.1}$$

Another way of computing LVEDP from IF and STI parameters may include using isovolumic contraction time (ICT). In this case the, Equations 4.1 and 5.1 can be written as:

$$LVEDP = K_3(IFs, ICT) \qquad \text{Eq. 6.1}$$

In an alternative, DBP can also be included with ICT:

$$LVEDP = K_4(IFs, ICT, DBP) \qquad \text{Eq. 7.1}$$

Combination of both ICT and PEP with the IFs may increase the accuracy of the LVEDP approximation, as follows:

$$LVEDP = K_5(IFs, ICT, PEP) \qquad \text{Eq. 8.1}$$

Once again, DBP can be included:

$$LVEDP = K_6(IFs, ICT, PEP, DBP) \qquad \text{Eq. 9.1}$$

In cases of valvular diseases such as mitral valve and aortic valve diseases, the sound wave can be used to correct for Equations 4.0-6.0 or 4.1-9.1. Advantages of approximating LVEDP using any of the methods described above include the ease of obtaining all the required input noninvasively, for example using portable devices.

The contractility feature (e.g., intrinsic frequencies or derivative) in Equations 4.1 through 9.1 can be obtained from measurements of carotid waveform, radial waveform, femoral waveform or pulse ox waveform. Depending on the location of measurement, the functions ($K_1$-$K_6$) may be different. In some embodiments, AoDP can be approximated by a brachial cuff pressure or any other noninvasive techniques for diastolic blood pressure measurement (DBP).

Intrinsic frequency is useful for revealing clinically relevant information about the dynamics of the left ventricle (LV), arterial system and their interactions. IF frequencies are operating frequencies based on the Sparse Time-Frequency Representation (STFR), treating the LV combined with the aorta and the remaining peripheral arteries as a coupled dynamical system (heart+aortic tree) which is decoupled upon closure of the aortic valve. Utilizing the IF method, a processor can extract two IF frequencies, ω1 and ω2 (along with other independent variables), from a single arterial blood pressure waveform. One important advantage of the IF method is that the absolute magnitude of the arterial pressure wave is not required to extract the IF parameters, only the waveform morphology (sometimes referred to herein as "waveform features"). As such, the IFs can be easily acquired noninvasively, instantaneously, and inexpensively using a smartphone or arterial applanation tonometry. The first IF, $\omega_1$, describes the dynamics of the systolic phase of the cardiac cycle where the LV and aorta (vasculature) are a coupled dynamic system. The second IF, $\omega_2$, is dominated by the dynamics of the vasculature.

Previous studies have indicated that ω1 is mainly determined by the LV contractility while $\omega_2$ is mostly determined by vascular function (e.g. arterial stiffness, arterial wave dynamics, and afterload). In a blind clinical study, it was shown LV ejection fraction (LVEF, a surrogate of LV contractility) derived using IF applied to carotid waveforms extracted using an iPhone, were similar to those measured from cardiac magnetic resonance imaging (CMRI) (r=0.74, P<0.00001). Importantly, a very strong correlation between LVEF measured by CMRI and LVEF computed by IF (LVEF-IF) was observed (r=0.94, p<0.0001) among HF patients. It has been demonstrated that detection of cardiac systolic dysfunction (as measured by LVEF) via the noninvasive LVEF-IF method was more accurate and sensitive than 2D echocardiography. In addition, central arterial stiffness (carotid-femoral pulse wave velocity (PWV)) can be computed using IF of a single noninvasively measured carotid pressure waveform (without any need for ECG measurement and/or femoral tonometry). Estimated PWV by IF method is equivalent to PWV measurements obtained by direct methods in predicting the risk for CVD. The IF method is a powerful tool for noninvasive ventricular performance (contractility) and vascular function (afterload) evaluation.

The present disclosure includes a discussion of a new systems-based approach, called Cardiac Triangle Mapping (CTM), for hemodynamic evaluation of the LV. This method uses pre-ejection period (PEP) and IF mathematics to compute LVEDP. Other, more general approaches without using IFs for approximation of LVEDP are also described.

The intrinsic frequency (IF) method models a dynamic system as an object rotating around an origin. The angular velocity of the rotation is the intrinsic frequency. In the coupled LV-aorta system, the average angular velocity of rotation (instantaneous frequency) during systole when LV and aorta are couple together is ω1. The average angular velocity during diastole when aorta gets decoupled from LV (after the closure of the aortic valve) is $\omega_2$. Simply put, the IF method assumes that the instantaneous frequency of a coupled dynamical system is piecewise constant in time with the step that occurs at the time of decoupling. In the LV-aorta system, the decoupling time is the time of the closure of the aortic valve. From the definition, IF frequencies are fundamentally different than Fourier harmonics or any other resonance-type frequencies. The mathematical formulation of IF method is as follows:

$$\text{Minimize:} \| p(t) - X(0, T_0[(a_1 \cos(\omega_1 t) + b_1 \sin(\omega_1 t)] - X(T_0, T)[(a_2 \cos(\omega_2 t) + b_2 \sin(\omega_2 t)] - c \|_2^2 \qquad (9.2)$$

This L2 minimization is subject to continuity at T0 (time of the decoupling=time of the dicrotic notch) and periodicity of the waveform. Here, χ(a, b) is the indicator function (χ(a, b)=1 if a≤t≤b and χ(a, b)=0 otherwise) and p(t) is the arterial waveform. a1, a2, c, b1, b2, ω1, and ω2 are the unknowns that can be found by solving this nonconvex minimization problem.

Referring to FIG. 3, aspects of a method 300 for applying the foregoing computational process for diagnosis and therapy summarizes use of the apparatus and computer-implemented methods described in more detail below. Except for the operations 318, 320, any one or more of the diagrammed operations of the method 300 may be performed automatically using an LVEDP measurement apparatus as described herein.

Figure 2B:
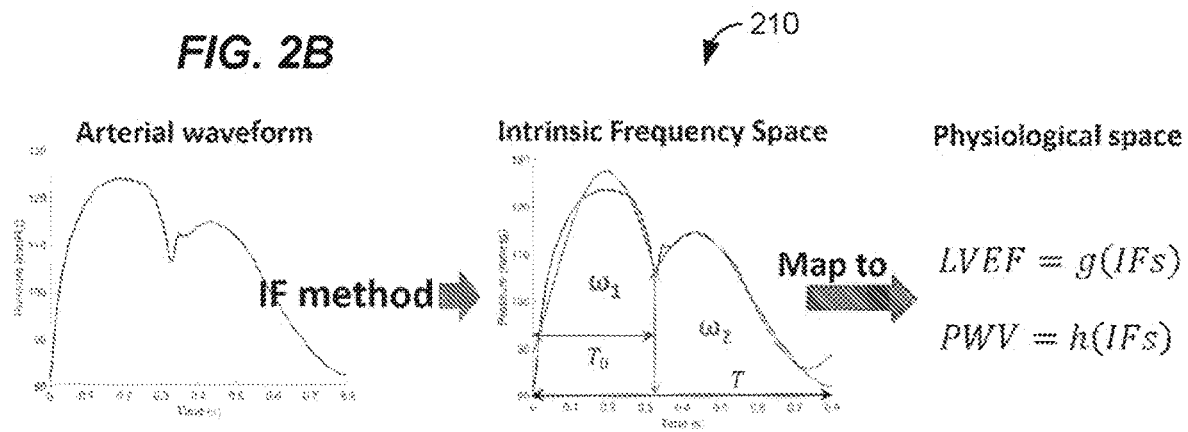

The IF method uses the information stored in an arterial waveform (e.g. carotid waveform) and creates a multidimensional IF space. These dimensions include the ω1 and ω2, duration of the cycle and the coordinates of the decoupling point. The decoupling coordinates are represented as relative height of decoupling at the dicrotic notch (RHDN) and time of decoupling at the dicrotic notch (T0). Previous studies have indicated that LVEF (surrogate of LV contractility), LV-arterial coupling optimality, and central pulse wave velocity (a major determinant of arterial impedance and pulsatile afterload) can be evaluated as function of IF parameters (FIG. 2B). Previous results indicate that LV contractility and afterload can be approximated as a function of IFs (ω1, ω2, . . . ). Therefore, without loss of generality, we can represent LV contractility and afterload as functions of ω1 and ω2.

$$Ctr \approx f_1(\omega_1, \omega_2), \qquad (9.3)$$

$$AL \approx f_2(\omega_1, \omega_2), \qquad (9.4)$$

Referring to chart series 210 of FIG. 2B, IF creates a 5-dimensional IF space from a pressure waveform, with ω1, w 2, T0, RHDN (vertical double-headed arrow divided by the total range), and T as the dimensions. The representative value in IF space can then be mapped to physiological space where LVEF (a surrogate for Ctr) and central pulse wave velocity (PWV) can be computed.

Figure 2C:
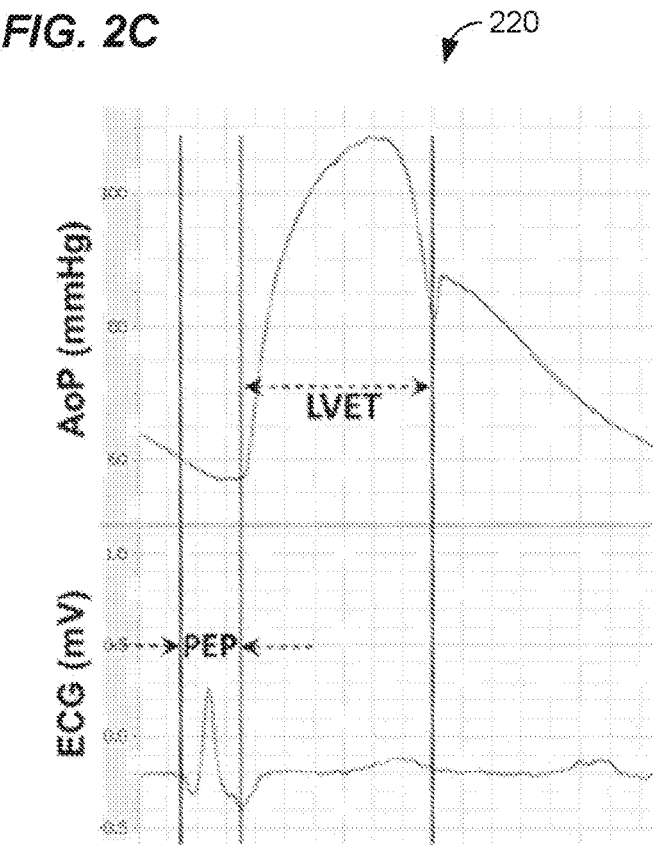

Systolic time interval (STI) method was first introduced in the 1960s. Clinical studies have shown that LV function performances such as contractility and preload can be approximated under certain conditions using STI methods. Two major components of the STI method are LV ejection time (LVET) and pre-ejection period (PEP). LVET is the time interval from the opening of the aortic valve to the closure of the aortic valve marked by the dicrotic notch (note that LVET is the same as T0 in the IF method). PEP is the time interval from the beginning of the QRS complex to the opening of the aortic valve. QRS complex is a combination of Q wave, R wave, and S wave from ECG where Q wave is any downward deflection immediately after the P wave, R wave is an upward deflection after Q wave, and the S wave is a rapid downward deflection after the R wave. Previous studies have shown that LV preload is inversely proportional to PEP at a given LV contractility and afterload. Chart 220 of FIG. 2C shows how PEP is measured from simultaneous pressure waveform and electrocardiogram (ECG). Two major systolic time interval components, pre-ejection period (PEP) and LV ejection time (LVET) are shown. PEP is the time interval from the beginning of the QRS complex to the opening of the aortic valve. LVET is the time interval from the opening of the aortic valve to the closure of the aortic valve marked by the dicrotic notch. The upper waveform is the aortic pressure waveform (AoP) and the lower waveform is the ECG waveform.

Further, more detailed aspects of the cardiac triangle method are discussed in connection with FIGS. 2D—below. Cardiac Triangle Mapping (CTM) is based on the fact that ventricular function is modulated by three factors: (i) the contractile state of the myocardium or contractility, (ii) the afterload that is related to vascular function and LV-arterial coupling, and (iii) the preload, which can be quantified by LVEDP.

IF parameters such as $\omega_1$ and $\omega_2$ are extracted from the arterial waveforms. These waveforms are the result of interactions between LV contractility and vascular function (resistance, compliance, LV-aorta coupling); therefore, they carry little or no information about the state of the LV preload. This means that PEP provides information that cannot be retrieved from IFs ($\omega_1$ and $\omega_2$). At a fixed LV contractility and afterload, PEP changes (inversely) as preload change. Since PEP is related to LV preload while $\omega_1$ and $\omega_2$ are not, PEP should be orthogonal (or at very least not parallel) to $\omega_1$ and $\omega_2$ (and other IF dimensions). As a result, a combination of IFs ($\omega_1$ and $\omega_2$) and PEP creates a complete set that can map LV dynamics, and subsequently provide information about the hemodynamics of LV. The CTM hypothesis states that $\omega_1$ and $\omega_2$, PEP map the global ventricular function. All LV-related mechanical biomarkers such as LVEDP can be computed as a function of IFs (e.g. $\omega_1$, $\omega_2$) and PEP. Mathematical expressions are provided in Eqs. 2.1-9.1 above.

The state of LV performance is defined by Ctr, AL, and preload; therefore, it can geometrically be represented as a triangle ($\triangle ABC$ in FIG. 2D). For the purposes of this manuscript, we will refer to it as cardiac triangle. Inspired by the shape of the pressure and ECG waveforms in a cardiac cycle (FIG. 2D), and without loss of generality, we assume the cardiac triangle is a right triangle where PEP is one leg (AC), afterload minus LVEDP is the other leg (BC), and the slope of the AB line is Ctr (in other words, the tangent inverse of Ctr is the angle $\angle A$). This choice of Ctr is in agreement with past studies that showed LV dp/dtmax is a measure of contractility (FIG. 2D). In our assumption, the nonlinear curves from point A to point B and A to C are approximated as straight lines. The error associated with assuming AB and AC as straight lines can be reduced by appropriate usage of nonlinear parameters such as $\omega_1$. According to the triangle of FIG. 2D, the relationship of Eq. 1 derives. The graph 230 of FIG. 2D show the cardiac tringle shape inspired by the shape of LV pressure, aortic pressure, and ECG waveform. Uppermost waveform in the graph is LV pressure, slightly underneath it in the graph is aortic pressure, and lowest waveform in the graph is ECG. ECG was scaled and adjusted for better visualization.

Physiological or physical parameters such as LV contractility, arterial diastolic pressure, LVEDP, etc. are the edges, angles, or vertices of the cardiac triangle (FIG. 2E). As described in the previous paragraph, the edges are not necessarily straight. The edges can be curvilinear as shown in graph 240, FIG. 2E. A triangle formed by $\omega_1$, $\omega_2$, and PEP (the "IF-triangle") can also define the full state of LV performance hence allowing for computation of LVEDP. This is based on a simple law of geometry: by knowing three components (e.g. three sides or two sides+one angle), the whole triangle can be solved. Without loss of generality, IF-triangle can be considered as a triangle with straight sides as shown in graph 250 since IF parameters (e.g. $\omega_1$ and $\omega_2$) carry non-linearities associated with the LV-aorta system. FIG. 2E shows a schematic 240 of a generalized cardiac triangle mapping (CTM), at 250 shows a simplified IF-based CTM with straight edges. Ctr is LV contractility and tan−1 is tangent inverse. Derivation of a solution for LVEDP in view of the cardiac triangle is given above (Eqs. 2.1-4.1). An explicit version of Eq. 4.1 is given below:

$$\text{LVEDP} = f_2(\omega_1,\omega_2) - f_1(\omega_1,\omega_2) \times PEP \tag{9.5}$$

Data indicates that $\omega_1$ corrected with the LV ejection time ($\omega_1 \sqrt{T_o}$, where $T_o$ is the LVET) is strongly correlated with LVEF. Therefore, by introducing a minor error, we can replace $f_1$(or Ctr) in equation 9.5 with LVEF/$\sqrt{T_o}$. Aortic diastolic pressure (AoDP) may also be a surrogate for AL). Hence, Equation 9.5 is simplified to:

$$LVEDP = c_1 AoDP - c_2 \frac{LVEF \times PEP}{\sqrt{T_o}} \tag{9.6}$$

Here, c1 is a unitless constant and c2 is a constant with a unit of mmHg/$\sqrt{\text{second}}$. Linear multiple regression may be used to compute the best value for c1 and c2.

Referring to FIG. 3, aspects of a method 300 for applying the foregoing computational process for diagnosis and therapy summarizes use of the apparatus and computer-implemented methods described in more detail below. Except for the operations 318, 320, any one or more of the diagrammed operations of the method 300 may be performed automatically using an LVEDP measurement apparatus as described herein.

At 302, the operator determines whether the patient is diagnosed with or has symptoms of a valvular disease, for example, mitral valve and aortic valve diseases. If so, at 308, the operator may collect a heart sound waveform, for example, by using a digital stethoscope.

Whether or not valvular disease is indicated, at 304, an operator captures at least one hemodynamic pulse waveform from a patient using any suitable method described below. For example, the hemodynamic pulse waveform may be, or may include, any one or more of a carotid pressure waveform, aortic wall waveform, carotid vessel wall waveform, radial pressure waveform, radial vessel wall waveform, brachial pressure waveform, brachial vessel wall waveform, femoral pressure waveform, femoral vessel wall waveform, or pulse oximeter (pulsOx) waveform. Non-invasive equipment for collecting hemodynamic pulse waveform may include, for example, tonometry devices that can sense pressure waveform, microwave devices that can sense vessel wall motion, echo ultrasound devices that can sense vessel wall motion, or a pulseOx device for obtaining a pulseOx waveform.

Likewise, at 306, the operator captures an ECG waveform, for example, by applying an ECG device including an electrode array to the patient. The operations 302, 306 and 308 (if called for) are performed contemporaneously and the resulting waveform is time-delimited so simultaneous portions of different waveforms can be examined and analyzed for computation of an LVEDP approximation.

At 310, the operator provides the pulse waveform to a computing device for computation of a contractility feature (e.g., IF or a derivative of the waveform). IF may be computed for example by a STFR method referenced herein above. In addition, at 312 the operator provides the pulse and ECG waveforms to the computing device for computation of at least one STE parameter, PEP and/or ICT. If valvular disease is indicated, at 314 the operator may adjust parameters used to compute the LVEDP based on the heart sound waveform, for example, any parameters that depend on the time that the PEP begins or ends.

At 316, the operator may compute LVEDP using any one of Equations 4.0-6.0 or 4.1-9.1 described herein above. Optionally, at 318, the operator may confirm the LVEDP approximated in block 316 with an LVEDP determined from traditional invasive procedures. Data from the invasive procedures may be used to calibrate sensor data for the patent so that future non-invasive LVEDP determination is more accurate. At 320, the operator considers, recommends and/or adjusts a therapeutic or preventative plan based on the LVEDP or changes therein.

Figure 4:
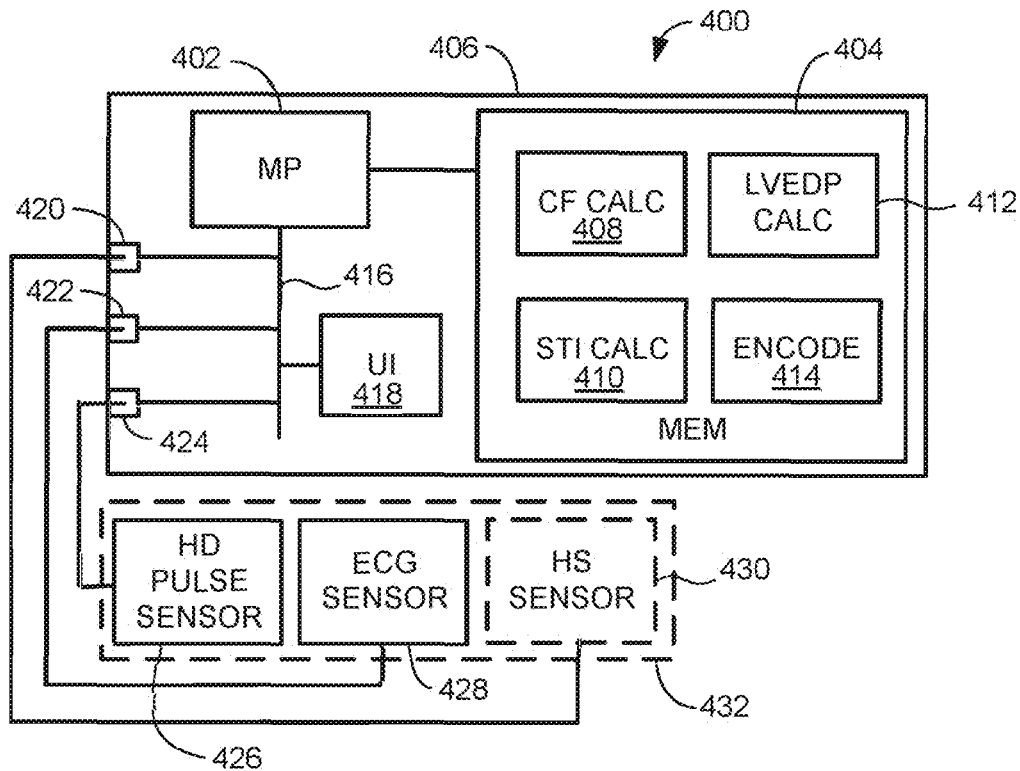
FIG. 4 is a block diagram illustrating an apparatus for non-invasive approximation of LVEDP.

In many contexts the user will make use of a programmable device configured for performance of the technical steps and method disclosed herein. FIG. 4 shows an example of an LVEDP apparatus 400 in block diagram form. The apparatus 400 includes at least one processor 402 coupled to a memory 404, for example, a random access memory (RAM) holding program instructions and data for rapid execution or processing by the processor during execution of methods as described herein. When the apparatus 400 is powered off or in an inactive state, program instructions and data may be stored in a long-term memory, for example, a non-volatile magnetic, optical, or electronic memory storage device, remote server, remote cloud storage or distributed ledger (not shown). Either or both of the RAM 404 or a long-term memory may comprise a non-transitory computer-readable medium holding program instructions, that when executed by the processor 402, cause the apparatus 400 to perform a method or operations as described herein. Program instructions may be written in any suitable high-level language, for example, C, C++, C #, or Java™, and compiled to produce machine-language code for execution by the processor. Program instructions may be grouped into functional modules 408-412, to facilitate coding efficiency and comprehensibility. It should be appreciated that such modules, even if discernable as divisions or grouping in source code, are not necessarily distinguishable as separate code blocks in machine-level coding. Code bundles directed toward a specific function may be considered to comprise a module, regardless of whether or not machine code on the bundle can be executed independently of other machine code. In other words, the modules may be high-level modules only.

The LVEDP apparatus 400 may be enclosed or mounted in a housing, package, and/or circuit board 406, together with other components, for example a user interface device 418 coupled to the processor 402 by a bus 416. A user interface device may be, or may include, a touchscreen, keypad, microphone/audio transducer system, head-mounted display with eye tracking, or other device for providing information to a user and receiving user input. Input ports 420, 422, 424 may also be coupled to the processor 402 via the bus 416 or other coupling. Examples of input ports 420, 422, 424 include universal serial bus (USB), a Lightning™ connector port by Apple™, a serial port, an audio port, wireless receiver, or any other useful input port or internal connection/bus for receiving waveform data from sensors 426, 428, 430. The sensors 426, 428, 430 may be housed in a separate sensor module 432, may be freestanding, independent sensor devices, or may be integrated in or on the housing, package, and/or circuit board 406 with the processor 402 and memory. In some embodiments, a portable sensor component containing at least a hydrodynamic pulse waveform sensor 426 and ECG sensor 428 are packaged in a small package 432 that can be held against the patient's skin over the carotid or other artery, and is coupled wirelessly (e.g., using a Bluetooth connection) to a smartphone, notepad computer, laptop computer or similar portable device holding the processor 402, memory 404 and user interface 418.

The hemodynamic waveform sensor 426 may be, or may include, an optical sensor that can measure vessel wall motion, a tonometry device that can measure pressure waveform or movement at the skin surface, a microwave device that can measure vessel wall motion and ECG signals for PEP and/or ICT measurement, or an echo ultrasound device that can measure vessel wall motion. For semi-invasive and beat-to-beat evaluation of LVEDP in hospital or clinic environments, the sensor 426 may be, or may include, implanted pressure sensors in the aorta, or inline and invasive radial or femoral catheters.

The ECG sensor 428 may be, or may include, a smartphone application and system with ECG ability that can be used to measure pulse waveform for IF parameters, PEP, and STI computation using an electrode array, or an ECG system. A heart sound sensor 430 may be, or may include, a digital stethoscope. Other useful sensors for providing waveform data to the processor 402 may be, or may include, a cuff pressure measurement device for DBP measurement, or a pulseOx device for pulseOX waveform measurement. Examples of a packaged sensor assembly 432 are provided by portable electronic hemodynamic sensor systems as described by Rinderknecht, Pahlevan et, al in U.S. Pat. No. 9,026,193.

Functional modules held in the memory 404 may include, for example, a contractility feature module 408 for calculating a contractility feature (e.g., intrinsic frequencies or a derivative of the waveform) based on hemodynamic waveform data as described herein, and an STI calculation module 410 for calculating at least one of a PEP or ITC from ECG and/or heart sound waveform data as described herein. The memory may further hold a LVEDP calculation module 412 for calculating LVEDP using any one or more of Equations 4.0-6.0 or 4.1-9.1. The memory may further hold an encoding module 414 for encoding one or more LVEDPs calculated by module 412 for at least one of storage, transmittal, or output in human-comprehendible form by UI 418 or other user interface device. The memory 404 may hold other functional modules as generally known in the computing arts for routine functionality. Other aspects of the LVEDP apparatus 400 may be as described in connection with the apparatus 1000 shown in FIG. 10 or 13.

In accordance with the foregoing, and by way of additional example, FIG. 5 shows aspects of a method 500 according to an embodiment for performance by an LVEPD-estimating apparatus 400, 1000 as described herein. Referring to FIG. 5, a computer-implemented method 500 for approximation of left ventricular end diastolic pressure (LVEDP) using non-invasive sensors coupled to a computing apparatus may include, at 510, receiving by at least one processor of the computing apparatus hemodynamic waveform data from a non-invasive sensor coupled to a patient. The waveform data may include, for example carotid pressure waveform. As an alternative to carotid pressure waveform, or in addition, receiving the waveform data 510 may include receiving aortic wall waveform, carotid vessel wall waveform, radial pressure waveform, radial vessel wall waveform, brachial pressure waveform, brachial vessel wall waveform, femoral pressure waveform, femoral vessel wall waveform, or pulse oximeter (pulsOx) waveform. In some embodiments, non-invasively measured ejection fraction (EF) and fractional shortening (FS) from echo, CTScan or MRI can be used as a surrogate of IF parameters. As an alternative, the contractility feature (e.g. intrinsic frequencies) of flow or velocity waveforms instead of pulse or pressure waveforms can be used in Equations 2.0-6.0 or 2.1-9.1.

In an aspect of the operation 510 relating to determination of PEP or ICT, a processor of client device for providing an LVEDP output may approximate IF parameters can be approximated using one or more of the following approaches: using simultaneously measured sound waveform at the heart and ECG; using simultaneously measured sound waveform at the carotid artery and ECG; using simultaneously measured sound waveform at heart and carotid waveform (Pressure, wall displacement, or flow/velocity); using simultaneously measured ECG and carotid waveform (Pressure, wall displacement, or flow/velocity); using simultaneously measured ECG and aortic flow waveform (e.g. in a cardiac MRI or Echocardiogram setting); using simultaneously measured ECG and aortic wall displacement waveform; using simultaneously measured ECG and brachial waveform (Pressure, wall displacement, or flow/velocity); using simultaneously measured ECG and radial waveform (Pressure, wall displacement, or flow/velocity); using simultaneously measured ECG and femoral waveform (Pressure, wall displacement, or flow/velocity, or using simultaneously measured ECG and pulseOx waveform.

The method 500 may further include at 520 receiving, by the at least one processor, electrocardiogram (ECG) data or heart sound waveform data from a second non-invasive sensor coupled to the patient. In some cases, the method includes using the heart sound waveform data to correct or confirm an ECG waveform. The method 500 may further include at 530 determining, by the at least one processor, at least one of a pre-ejection period (PEP) or an isovolumic contraction time (ICT), based on simultaneous portions of the hemodynamic waveform data and at least one of the ECG data or the heart sound waveform data, for example as described in connection with FIG. 2. The method 500 may further include at 540 calculating, by the at least one processor, an LVEDP based on a contractility feature and at least one of the PEP and the ICT. The method 500 may further include at 550 encoding the LVEDP as digital data for at least one of storage, transmission, or human-comprehensible output.

Referring to FIGS. 6-9, the method 500 may include any one or more additional operations 600, 700, 770, 800 and 900 as described above and below herein. Each of these additional operations is not necessarily performed in every embodiment of the method, and the presence of any one of the operations does not necessarily require that any other of these additional operations also be performed.

Figure 6:
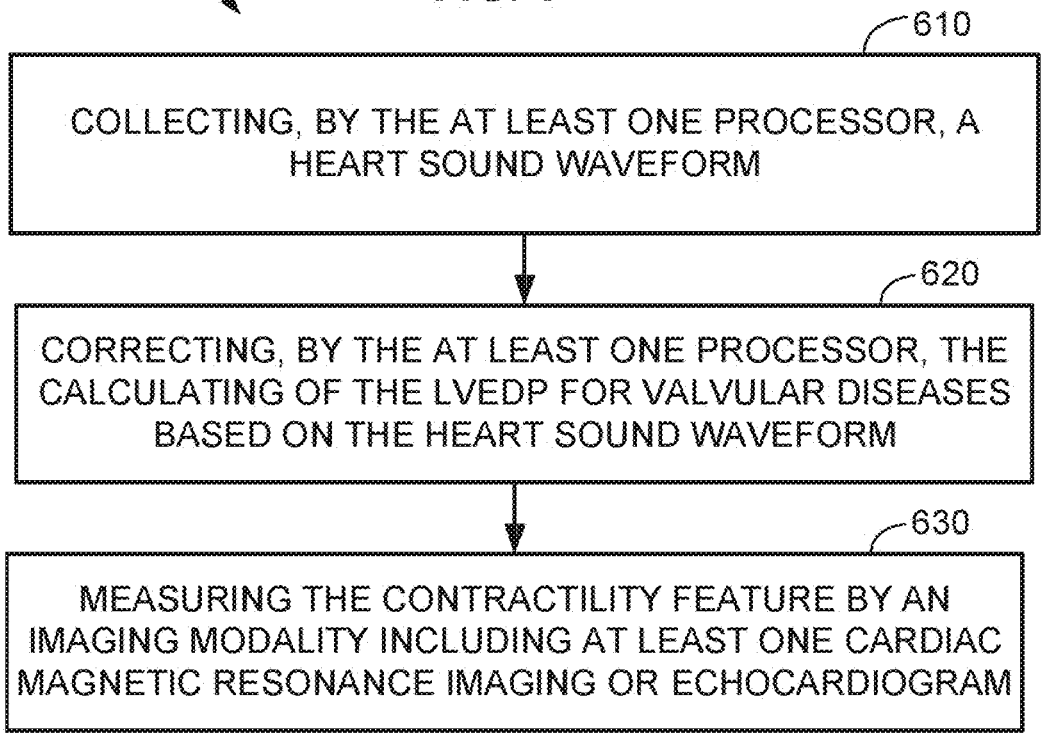

For example, referring to FIG. 6, method 500 may further include, at 610, collecting a heart sound waveform, for example, using a digital stethoscope. In some embodiments, the waveform data may be, or may include, heart sounds. In such cases, the method may further include, at 620, correcting the calculating of the LVEDP for valvular diseases based on the heart sound waveform. In an alternative aspect, the method 500 may include at 630, measuring, by the at least one processor, the contractility feature by an imaging modality including at least one cardiac magnetic resonance imaging (e.g. ejection fraction or fractional shortening) or echocardiogram (e.g. ejection fraction, fractional shortening, or myocardial strain). The imaging modality may be used as a source of the contractility feature of the patient, in lieu of, or in addition to, measuring the contractility feature based on the hemodynamic waveform data.

Figure 7:
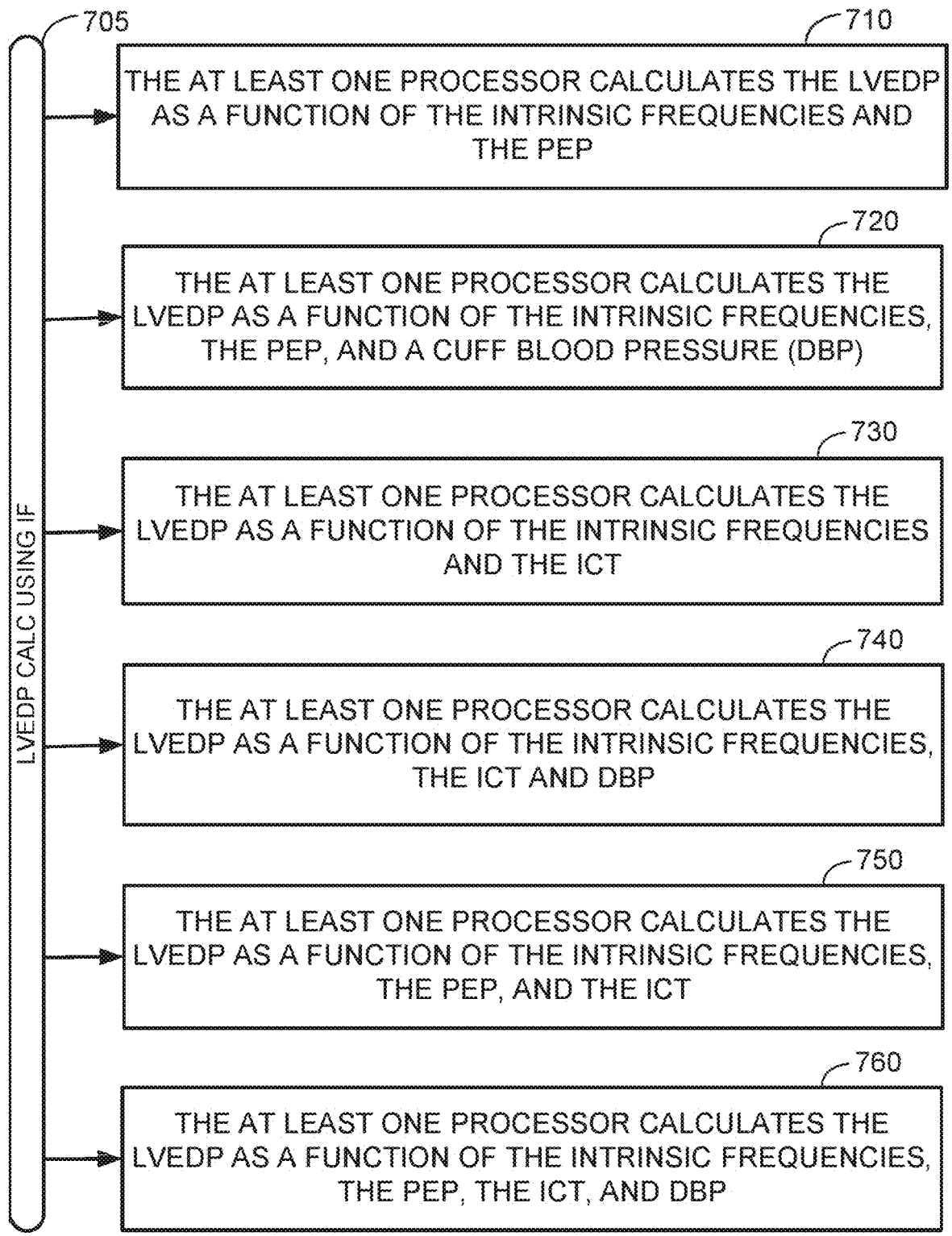

Referring to FIG. 7A, in related, alternative aspects the method 500 may include, at 705, calculating, by the at least one processor, intrinsic frequencies (as a specific cases of a contractility function) based on the hemodynamic waveform data, for example as described in the '193 Patent referenced herein. The at least one processor may calculate the LVEDP using any one or more of the Equations 4.1-9.1 For example, at 710 the processor may calculate LVEDP as a function of the intrinsic frequencies and the PEP using Equation 4.1. In an alternative, or in addition, at 720 the processor may calculate LVEDP as a function of the intrinsic frequencies, the PEP, and a cuff blood pressure (DBP) using Equation 5.1. In an alternative, or in addition, at 730 the processor may calculate LVEDP as a function of the intrinsic frequencies and the ICT using Equation 6.1. In an alternative, or in addition, at 740 the processor may calculate LVEDP as a function of the intrinsic frequencies, the ICT, and a DBP, using Equation 7.1. In an alternative, or in addition, at 750 the processor may calculate LVEDP as a function of the intrinsic frequencies, the PEP, and the ICT, using Equation 8.1. In an alternative, or in addition, at 760 the processor may calculate LVEDP as a function of the intrinsic frequencies, the PEP, the ICT, and a DBP, using Equation 9.1. The alternative calculation methods shown in FIG. 7 may be summarized as calculating the LVEDP as a function of the intrinsic frequencies, at least one of the PEP and the ICT, and optionally a cuff blood pressure (DBP).

FIG. 7B shows a more general expression of which the alternatives shown in FIG. 7A are a special case. At 780, the method 500 may further include calculating the contractility feature based on the hemodynamic waveform data. The contractility feature may be, or may include, intrinsic frequencies, a derivative of the wave function, or other measure based on time and waveform features of the hemodynamic waveforms. At 790, the method 500 may include, for example, the at least one processor calculating the LVEDP as a function of the contractility feature, at least one of the PEP and the ICT, and optionally a DBP.

Referring to FIG. 8, in some embodiments, the method 500 may include at 810 determining a pulse wave velocity from the hemodynamic waveform data. At 820, the method may further include calculating the at least one of the PEP and the ICT using the pulse wave velocity to improve accuracy. Methods for calculating pulse waveform velocity are known in the art. More accurate information regarding pulse wave velocity will enable one of ordinary skill to form a more accurate estimate of PEP or ICT by correlating received waveforms with cardiac action by accounting for differences in signal lag. This may be useful in cases where a pulseOx waveform is being used. In such cases, the corresponding pulse wave velocity can be used to improve the accuracy of PEP measurement or estimation. In addition, where pulse waveforms are being captured at carotid, radial, brachial, or femoral locations, the corresponding pulse wave velocity is likewise useful to improve the accuracy of PEP measurement.

Referring to FIG. 9 at 910, in an aspect of the method 500, calculating the contractility feature (e.g., intrinsic frequencies or derivatives of the waveform) may be based on at least one of: carotid pressure waveform, aortic wall waveform, carotid vessel wall waveform, radial pressure waveform, radial vessel wall waveform, brachial pressure waveform, brachial vessel wall waveform, femoral pressure waveform, femoral vessel wall waveform, or pulsOx waveform. In a further aspect of the method 500, at 920, calculating the contractility feature may be based on at least one of: calculating a surrogate from non-invasively measured ejection fraction (EF) and fractional shortening (FS). In a related aspect of the method 500 at 930, calculating the contractility feature may be based on at least one of a flow or velocity waveform.

FIG. 10 is a conceptual block diagram illustrating components of an apparatus or system 1000 for approximation of left ventricular end diastolic pressure (LVEDP) as described herein, according to one embodiment. As depicted, the apparatus or system 1000 may include functional blocks that can represent functions implemented by a processor, software, or combination thereof (e.g., firmware).

As illustrated in FIG. 10, the apparatus or system 1000 may comprise an electrical component 1002 for receiving hemodynamic waveform data from a non-invasive sensor coupled to a patient. The component 1002 may be, or may include, a means for said receiving. Said means may include the processor 1010 coupled to the memory 1016, and to the first sensor 1014 comprising a non-invasive hemodynamic sensor as described herein, the processor executing an algorithm based on program instructions stored in the memory. Such algorithm may include a sequence of more detailed operations, for example, initiating a communication session with the first sensor 1014, correlating a waveform from sensor 1014 with respect to a time datum, and encoding one or more characteristic features of a received waveform from the sensor 1014 during the session in a computer memory using a numeric scheme.

The apparatus or system 1000 may further comprise an electrical component 1003 for calculating a contractility feature (e.g., intrinsic frequencies or derivative) based on the hemodynamic waveform data. The component 1003 may be, or may include, a means for said calculating. Said means may include the processor 1010 coupled to the memory 1016, the processor executing an algorithm based on program instructions stored in the memory. Such algorithm may include a sequence of more detailed operations, for example, calculating intrinsic frequencies as described in the '193 Patent, or taking a derivative of the input waveform.

The apparatus or system 1000 may further comprise an electrical component 1004 for receiving at least one of electrocardiogram (ECG) data or heart sound waveform data from a second non-invasive sensor coupled to the patient. The component 1004 may be, or may include, a means for said receiving. Said means may include the processor 1010 coupled to the memory 1016, and to the second sensor 1015 comprising an ECG or heart sound sensor, the processor executing an algorithm based on program instructions stored in the memory. Such algorithm may include a sequence of more detailed operations, for example, initiating a communication session with an ECG device or digital stethoscope, correlating a waveform from the ECG device or digital stethoscope with respect to a time datum, and encoding one or more characteristic features of a received waveform in a computer memory using a numeric scheme.

The apparatus or system 1000 may further comprise an electrical component 1005 for determining at least one of a pre-ejection period (PEP) or an isovolumic contraction time (ICT), based on simultaneous portions of the hemodynamic waveform data and at least one of the ECG data or the heart sound waveform data. The component 1005 may be, or may include, a means for said determining. Said means may include the processor 1010 coupled to the memory 1016, the processor executing an algorithm based on program instructions stored in the memory. Such algorithm may include a sequence of more detailed operations, for example, calculating a PEP as described in connection with FIG. 2 above by taking a time difference between initiation and termination of a pre-ejection period from characteristic waveforms.

The apparatus or system 1000 may further comprise an electrical component 1006 for calculating an LVEDP based on the contractility feature and at least one of the PEP and the ICT. The component 1006 may be, or may include, a means for said calculating. Said means may include the processor 1010 coupled to the memory 1016, the processor executing an algorithm based on program instructions stored in the memory. Such algorithm may include a sequence of more detailed operations, for example, executing operations for calculation of one or more of Equations 2.0-6.0 or 2.1-9.1 herein above.

The apparatus or system 1000 may further comprise an electrical component 1007 for encoding the LVEDP as digital data for at least one of storage, transmission, or human-comprehensible output. The component 1007 may be, or may include, a means for said encoding. Said means may include the processor 1010 coupled to the memory 1016, the processor executing an algorithm based on program instructions stored in the memory. Such algorithm may include a sequence of more detailed operations, for example, associating a binary value representing the LVEDP with a memory location, encoding a signal for an output device that produces a human-comprehensible output (e.g., a video, text, audio, or other output) including a representation of the LVEDP, and associating the encoded signal with the memory location.

The apparatus 1000 may optionally include a processor module 1010 having at least one processor, in the case of the apparatus 1000 configured as a data processor. The processor 1010, in such case, may be in operative communication with the modules 1002-1007 via a bus 1012 or other communication coupling, for example, a network. The processor 1010 may effect initiation and scheduling of the processes or functions performed by electrical components 1002-1007.

In related aspects, the apparatus 1000 may include a network interface module (not shown) operable for communicating with a storage device over a computer network. The first sensor 1014 may be, or may include, any non-invasive hemodynamic sensor as described herein. The second sensor 1015 may be, or may include, any non-invasive ECG or heart sound sensor as described herein.

In further related aspects, the apparatus 1000 may optionally include a module for storing information, such as, for example, a memory device/module 1016. The computer readable medium or the memory module 1016 may be operatively coupled to the other components of the apparatus 1000 via the bus 1012 or the like. The memory module 1016 may be adapted to store computer readable instructions and data for effecting the processes and behavior of the modules 1002-1007, and subcomponents thereof, or the processor 1010, or the method 500 and one or more of the additional operations 600-900 described in connection with the method 500. The memory module 1016 may retain instructions for executing functions associated with the modules 1002-1007. While shown as being external to the memory 1016, it is to be understood that the modules 1002-1007 can exist within the memory 1016.

Referring to FIG. 11, an alternative method 1100 for approximation of left ventricular end diastolic pressure (LVEDP) using non-invasive sensors coupled to a computing apparatus, may include operations as diagrammed in the Figures and/or described below. The method 1100 may include, at 1110, receiving, by at least one processor of the computing apparatus, hemodynamic waveform data from a non-invasive sensor coupled to a patient and at least one of electrocardiogram (ECG) data or heart sound waveform data from a second non-invasive sensor coupled to the patient. The method 1100 may further include at 1120 synchronizing, by the at least one processor, the hemodynamic waveform data and the at least one of electrocardiogram (ECG) data or heart sound waveform data. The method 1100 may further include at 1130 calculating, by the at least one processor, an LVEDP based on time features and waveform features of the hemodynamic waveform data and the at least one of electrocardiogram (ECG) data or heart sound waveform data. As used herein, "time features" refer to features characterized by a time point or time period, for example a time at which a waveform feature is marked, e.g., at a beginning, end, duration or middle. For example, an initiation time of a dicrotic notch or a PEP are time features. Also as used herein, "waveform features" are functions of a waveform, for example, a derivative, intrinsic frequencies, and other characteristics of the waveform in its characteristic space (e.g., time-pressure, time-displacement, time-amplitude, etc.).

Referring to FIGS. 12A-B and 6 the method 1100 may include any one or more additional operations 1200, 600 as described above and below herein. Each of these additional operations is not necessarily performed in every embodiment of the method, and the presence of any one of the operations does not necessarily require that any other of these additional operations also be performed.

In an aspect, the method 1100 may further include at 1210, encoding the LVEDP as digital data for at least one of storage, transmission, or human-comprehensible output. At 1220, the method 1100 may further include determining, by the at least one processor, at least one of a pre-ejection period (PEP) or an isovolumic contraction time (ICT), based on simultaneous portions of the hemodynamic waveform data and at least one of the ECG data or the heart sound waveform data. At 1230, the method 1100 may further include, by the at least one processor, calculating a contractility feature based on the hemodynamic waveform data. In an aspect, at 1240, the contractility feature may be, or may include, at least one of a derivative of the hemodynamic waveform data or intrinsic frequencies. At 1250, the method 1100 may further include, by the at least one processor, calculating the LVEDP as a function of the contractility feature, at least one of the PEP and the ICT, and optionally a cuff blood pressure (DBP).

Referring to FIG. 12B, the method 1100 may further include at 1260, calculating the time features and waveform features of the hemodynamic waveform data (HWD) and the at least one of electrocardiogram (ECG) data or heart sound waveform (HSW) data based on at least one of: carotid pressure waveform, aortic wall waveform, carotid vessel wall waveform, radial pressure waveform, radial vessel wall waveform, brachial pressure waveform, brachial vessel wall waveform, femoral pressure waveform, femoral vessel wall waveform, or pulseOx waveform. In an aspect, the method 1100 may further include, at 1270, calculating the time features and waveform features of the hemodynamic waveform data and the at least one of electrocardiogram (ECG) data or heart sound waveform data based on or supplemented with at least one of: calculating a surrogate from non-invasively measured ejection fraction (EF) and fractional shortening (FS). In another aspect, at 1280 the method 1100 may further include calculating the time features and waveform features of the hemodynamic waveform data and the at least one of electrocardiogram (ECG) data or heart sound waveform data based on or supplemented with at least one of a flow or velocity waveform.

Referring back to FIG. 6, in an aspect the hemodynamic waveform data is from heart sounds, and the method 1100 may further include, at 610 collecting the waveform data from the heart sounds. In addition, the method 1100 may further include, at 620, calculating of the LVEDP for valvular diseases based on the waveform data collected from the heart sounds. In another aspect, at 630, the method 1100 may further include measuring the contractility feature by an imaging modality including at least one cardiac magnetic resonance imaging or echocardiogram, in lieu of, or in addition to, deriving the contractility feature from waveform data. Other aspects of the method 1100 may be as described herein above generally, or in connection with the related method 500.

Figure 13:
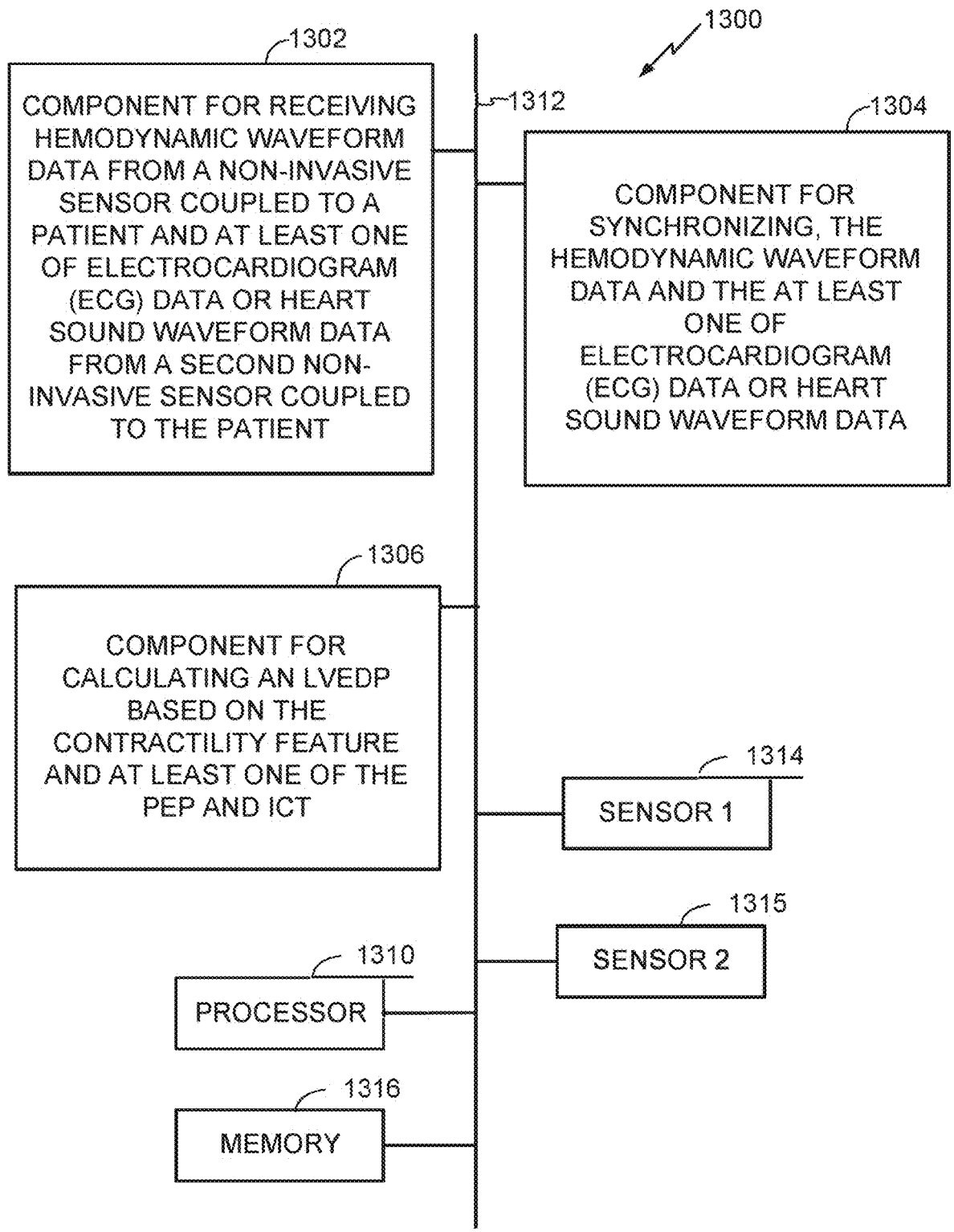
FIG. 13 is a conceptual block diagram illustrating components of an apparatus or system for non-invasive approximation of LVEDP using the method of FIG. 11.

In accordance with the foregoing, FIG. 13 is a conceptual block diagram illustrating components of an apparatus or system 1300 for approximation of left ventricular end diastolic pressure (LVEDP) as described herein, according to an alternative embodiment. As depicted, the apparatus or system 1300 may include functional blocks that can represent functions implemented by a processor, software, or combination thereof (e.g., firmware).

As illustrated in FIG. 13, the apparatus or system 1300 may comprise an electrical component 1302 for receiving hemodynamic waveform data from a non-invasive sensor coupled to a patient and at least one of electrocardiogram (ECG) data or heart sound waveform data from a second non-invasive sensor coupled to the patient. The component 1302 may be, or may include, a means for said receiving. Said means may include the processor 1310 coupled to the memory 1316, to the first sensor 1314 comprising a non-invasive hemodynamic sensor as described herein and to the second sensor 1315 comprising an ECG sensor, the processor executing an algorithm based on program instructions stored in the memory. Such algorithm may include a sequence of more detailed operations, for example, initiating communication sessions with the first sensor 1314 and sensor 1315, correlating waveform from the sensors 1314, 1315 with respect to a time datum, and encoding one or more characteristic features of a received waveform from the sensors 1314, 1315 during the session in a computer memory using a numeric scheme.

The apparatus or system 1300 may further comprise an electrical component 1304 for synchronizing the hemodynamic waveform data and the at least one of electrocardiogram (ECG) data or heart sound waveform data. The component 1304 may be, or may include, a means for said synchronizing. Said means may include the processor 1310 coupled to the memory 1316, and to the second sensor 1315 comprising an ECG or heart sound sensor, the processor executing an algorithm based on program instructions stored in the memory. Such algorithm may include a sequence of more detailed operations, for example, receiving separate waveforms from the sensors 1314, 1315 contemporaneously, determining a time difference (e.g., signal lag) caused by any one or more of communication, processing, or hemodynamical factors, if any, and if a time difference is determined, applying a correction factor to compensate for the difference. One compensated, or if no time difference is determined, the algorithm may include marking each waveform relative to a common time datum.

The apparatus or system 1300 may further comprise an electrical component 1306 for calculating an LVEDP based on time features and waveform features of the hemodynamic waveform data and the at least one of electrocardiogram (ECG) data or heart sound waveform data. The component 1306 may be, or may include, a means for said calculating. Said means may include the processor 1310 coupled to the memory 1316, the processor executing an algorithm based on program instructions stored in the memory. Such algorithm may include a sequence of more detailed operations, for example, executing operations for calculation of one or more of Equations 2.0-6.0 or 2.1-9.1 herein above.

The apparatus 1300 may optionally include a processor module 1310 having at least one processor, in the case of the apparatus 1300 configured as a data processor. The processor 1310, in such case, may be in operative communication with the modules 1302-1306 via a bus 1312 or other communication coupling, for example, a network. The processor 1310 may initiate and schedule the processes or functions performed by electrical components 1302-1306.

In related aspects, the apparatus 1300 may include a network interface module (not shown) operable for communicating with a storage device over a computer network. The first sensor 1314 may be, or may include, any non-invasive hemodynamic sensor as described herein. The second sensor 1315 may be, or may include, any non-invasive ECG or heart sound sensor as described herein.

In further related aspects, the apparatus 1300 may optionally include a module for storing information, such as, for example, a memory device/module 1316. The computer readable medium or the memory module 1316 may be operatively coupled to the other components of the apparatus 1300 via the bus 1312 or the like. The memory module 1316 may be adapted to store computer readable instructions and data for effecting the processes and behavior of the modules 1302-1306, and subcomponents thereof, or the processor 1310, or the method 1100 and one or more of the additional operations 1200, 600 described in connection with the method 1100. The memory module 1316 may retain instructions for executing functions associated with the modules 1302-1306. While shown as being external to the memory 1316, it is to be understood that the modules 1302-1306 can exist within the memory 1316.

Those of skill would further appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

RESULTS: Preliminary results for calculation of LVEDP are based on previously published data. Since pressure waveforms and as a result $\omega_1$ and $\omega_2$ were not available for the data, EF was used as a surrogate of $\omega_1$ and $\omega_2$:

$$EF = Y_1(\omega_1, \omega_2, T_o) \xrightarrow{yields} \begin{cases} \omega_1 = X_1(EF, T_o) \\ \omega_2 = X_2(EF, T_o) \end{cases} \quad (10)$$

This simply means that $$\text{LVEDP} = k_1(X_1(EF,T_o),PEP) = k_1(EF,T_o,PEP) \quad (11)$$

Therefore, existence of $k_1$ from the preliminary data will ensures the existence of $X_1$ (or $X_2$).

Since $\omega_1 \sqrt{T_o}$ is well correlated to EF based on our unpublished data, it can be replaced in Equation 3.1 that gives:

$$LVEDP = c_1 AoDP + c_2 \frac{EF \times PEP}{\sqrt{T_o}} \quad (12)$$

Figure 14:
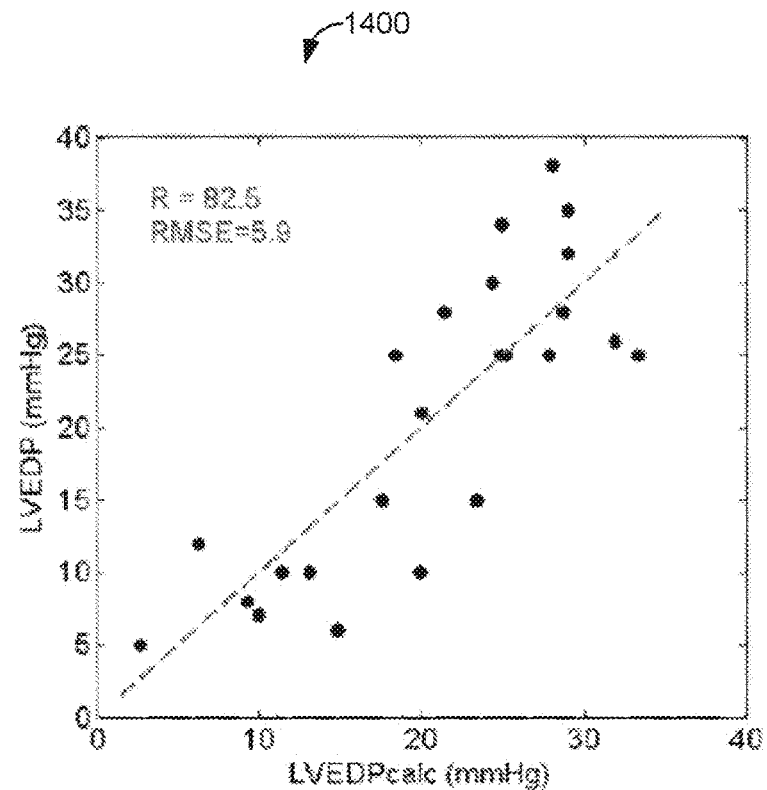
FIG. 14 is a chart illustrating approximation of LVEDP from AoDP, EF, PEP, and LV ejection time.

Results excluding valvular disease and Arrhythmia: Graph 1400 of FIG. 14 shows approximation of LVEDP from Equation 8.1 using AoDP, EF, PEP, and LV ejection time (T0). In order to test the hypothesis, 24 data points (excluding valvular disease and Arrhythmia) published by Garrard et al (Garrard C L, Weissler A M, Dodge H T (1970) The Relationship of Alterations in Systolic Time Intervals to Ejection Fraction in Patients with Cardiac Disease. Circulation 42: 455-462) was used to compute LVEDP using Equation 8.1. A multiple linear regression with two variable (two regressor) was applied to computer $c_0$, $c_1$, and $c_2$ and the intercept. The result shows R=82.5 (R-adjusted=80.5), Limit of agreement (LoA)=+-11.4, and root mean square error (RMSE)=5.68 mmHg.

As shown in FIG. 14, the model does not produce any false negative (LVEDPcalc<13 while LVEDP>13), and it only have one false positive (LVEDPcalc>13 while LVEDP<13).

Since EF is afterload dependent, LVEDP can also be approximated without AoDP as shown in Equation (9.6):

$$\boxed{LVEDP \propto \frac{EF \times PEP}{\sqrt{T_o}}} \quad (9.6)$$

With the same data set of Garrard et al, Equation 9.6 by itself shows 81.5 percent correlation with LVEDP.

Figure 15:
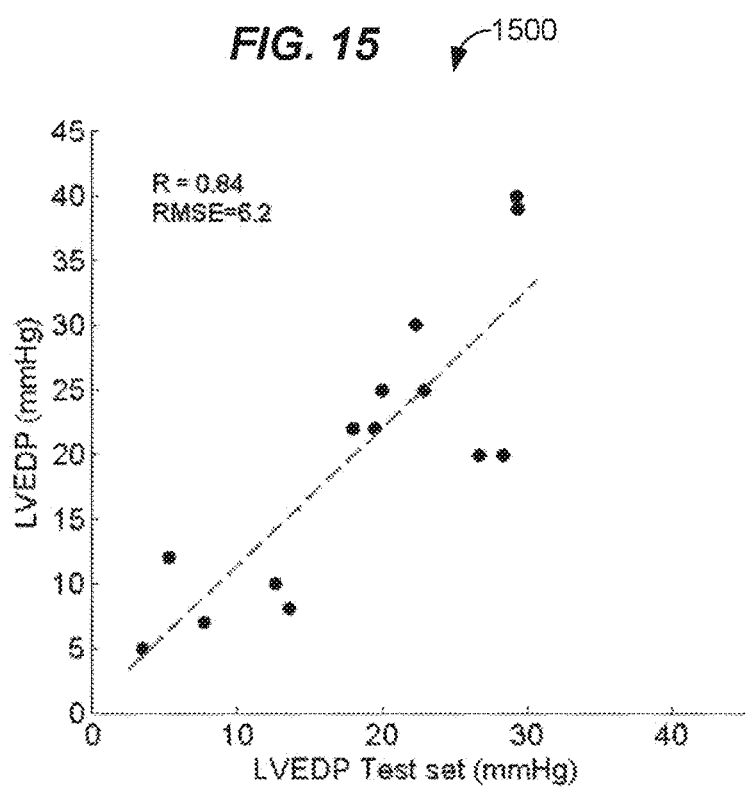
FIG. 15 is a chart illustrating approximation of LVEDP from linear regression using EF, PEP, and ejection time.
Figure 16:
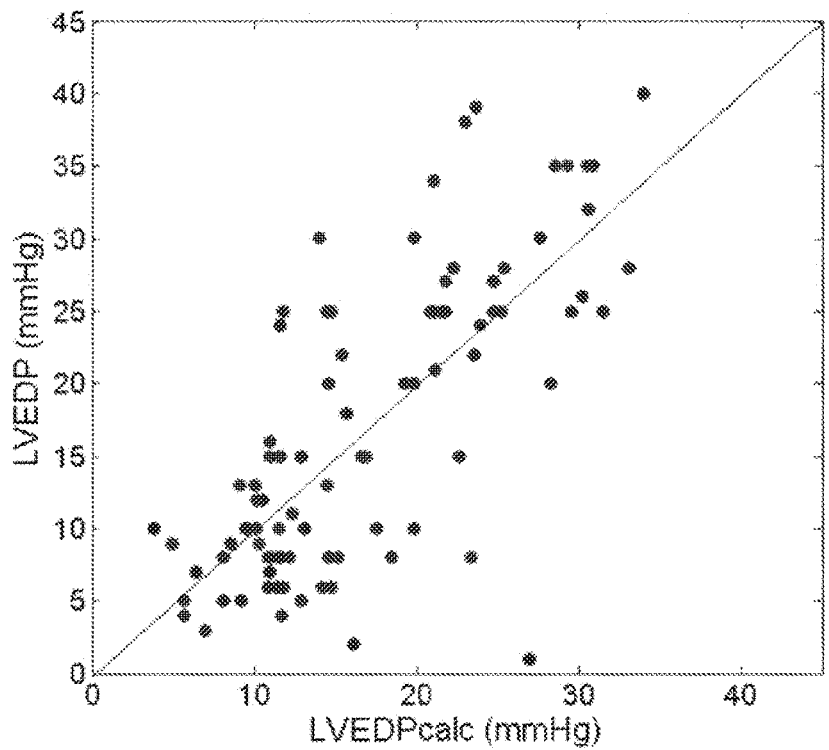
FIG. 16 is a chart illustrating approximation of LVEDP from multiple regression (interaction model) using EF, PEP, and ejection time.

Graph 1500 of FIG. 15 shows approximation of LVEDP from linear regression using EF, PEP, and ejection time (T0). Data was trained on 20 subjects and applied of 14 subjects presented here. In another data set that includes data of Garrard et al plus 10 subject data from Lewis et al (Lewis B S, Armstrong T G, Everson R C, Gotsman M S (1973) Predictive value of the systolic time intervals in primary myocardial disease. Chest 64: 431-438) that sums up to 34 data points, a linear multiple regression model (EF, PEP, and LVET as parameters) was trained on 20 data points and test on the other 14 subjects. The result shows R=0.84, LoA=+ 10-13.5 and RMSE=6.1 mmHg Graph 1600 of FIG. 16 shows approximation of LVEDP from multiple regression (interaction model) using EF, PEP, and ejection time (T0). Data includes subjects with valvular disease and arrhythmia.

Results including valvular disease and Arrhythmia: 93 data points (all data points) published by Garrard et al were used on a quadratic multiple regression model (parameters are PEP/LVET and EF that give 5 regressors) to approximate LVEDP. The result shows R=0.71 and LoA=+-13.7

Using interactions multiple regression between PEP, LVET and EF for LVEDP (6 regressor) gives R=0.74, LoA=+-13.3 and RMSE=6.8 mmHg.

Figure 17:
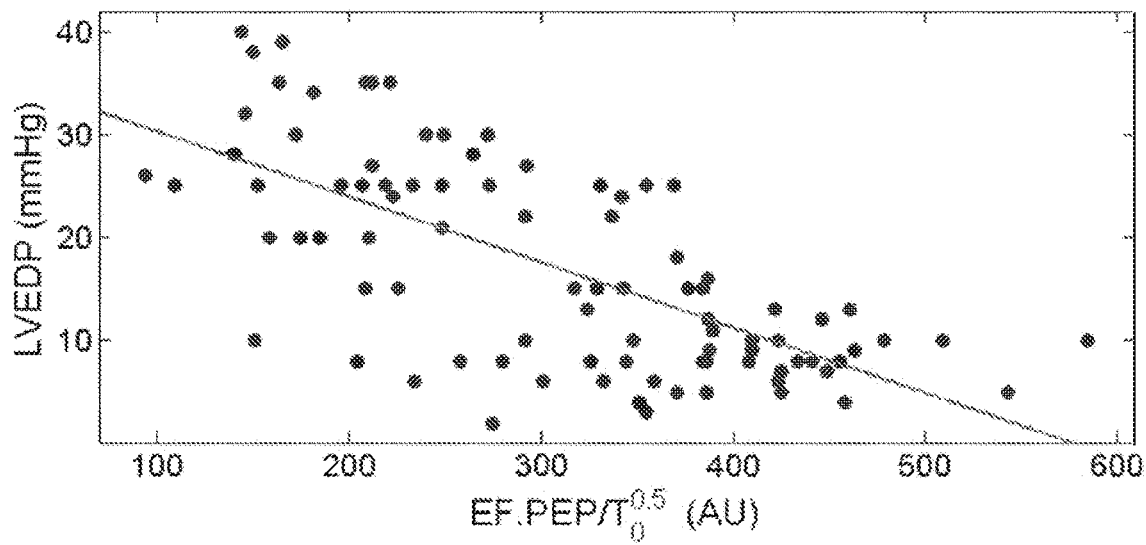
FIG. 17 is a chart illustrating Correlation between LVEDP and Equation (9).

Graph 1700 of FIG. 17 shows correlation between LVEDP and Equation (9)

$$\left(\frac{EF \times PEP}{\sqrt{LVET}}\right) \quad \text{Equation 9}$$

by itself shows 69 percent correlation with LVEDP, RMSE=7.4 mmHg.

GENERAL REMARKS: As used in this application, the terms "component", "module", "system", and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer or system of cooperating computers. By way of illustration, both an application running on a server and the server can be a component. One or more components may reside within a process and/or thread of execution and a component may be localized on one computer and/or distributed between two or more computers.

Various aspects are presented in terms of systems that may include a number of components, modules, and the like. It is to be understood and appreciated that the various systems may include additional components, modules, etc. and/or may not include all the components, modules, etc. discussed in connection with the figures. A combination of these approaches may also be used. The various aspects disclosed herein can be performed on electrical devices including devices that utilize touch screen display technologies and/or mouse-and-keyboard type interfaces. Examples of such devices include computers (desktop and mobile), smart phones, personal digital assistants (PDAs), and other electronic devices both wired and wireless.

In addition, the various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

Furthermore, the one or more versions may be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips . . . ), optical disks (e.g., compact disk (CD), digital versatile disk (DVD), BluRay™ . . . ), smart cards, solid-state devices (SSDs), and flash memory devices (e.g., card, stick). Of course, those skilled in the art will recognize many modifications may be made to this configuration without departing from the scope of the disclosed aspects.

In view of the exemplary systems described supra, methodologies that may be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described herein. Certain details are omitted from the drawings for illustrative simplicity, appearing only in the detailed description. Additionally, it should be further appreciated that the methodologies disclosed herein are capable of being stored on an article of manufacture to facilitate transporting and transferring such methodologies to computers.

The foregoing description is provided to enable any person skilled in the art to make or use the present disclosure. Various modifications to the disclosed aspects will be clear to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. A method for approximation of left ventricular end diastolic pressure (LVEDP) using data from non-invasive ECG and pressure sensors coupled to a computing apparatus, the method comprising:

receiving, by at least one processor of the computing apparatus, hemodynamic waveform data from a non-invasive pressure sensor coupled to a patient and electrocardiogram (ECG) data from a non-invasive ECG sensor coupled to the patient;

synchronizing, by the at least one processor, the hemodynamic waveform data and the ECG data; and calculating, by the at least one processor, an LVEDP based on time features and waveform features of the hemodynamic waveform data and the ECG data.

2. The method of claim 1, further comprising encoding the LVEDP as digital data for at least one of storage, transmission, or human-comprehensible output.

3. The method of claim 1, further comprising determining, by the at least one processor, at least one of a pre-ejection period (PEP) or an isovolumic contraction time (ICT), based on simultaneous portions of the hemodynamic waveform data and the ECG data.

4. The method of claim 3, further comprising calculating, by the at least one processor, a contractility feature based on the hemodynamic waveform data.

5. The method of claim 4, wherein calculating the LVEDP further comprises calculating the LVEDP as a function of the contractility feature, at least one of the PEP and the ICT, and optionally a cuff blood pressure (DBP).

6. The method of claim 4, wherein calculating the contractility feature comprises determining at least one of a derivative of the hemodynamic waveform data or intrinsic frequencies.

7. The method of claim 1, wherein calculating the time features and waveform features of the hemodynamic waveform data and the ECG data is based on at least one of: carotid pressure waveform, aortic wall waveform, carotid vessel wall waveform, radial pressure waveform, radial vessel wall waveform, brachial pressure waveform, brachial vessel wall waveform, femoral pressure waveform, femoral vessel wall waveform, or pulseOx waveform.

8. The method of claim 1, wherein calculating the time features and waveform features of the hemodynamic waveform data and the ECG data is based on or supplemented with at least one of a flow or velocity waveform.

9. An apparatus configured to approximate left ventricular end diastolic pressure (LVEDP) using data from non-invasive ECG and pressure sensors, comprising: at least one processor coupled to a memory, to a non-invasive hemodynamic waveform pressure sensor, and to a non-invasive electrocardiogram (ECG) sensor, wherein the memory holds program instructions that when executed by the at least one processor cause the apparatus to: receive hemodynamic waveform data from the non-invasive hemodynamic waveform pressure sensor and ECG data from the non-invasive ECG sensor; synchronize, the hemodynamic waveform data and the ECG data; and calculate an LVEDP based on time features and waveform features of the hemodynamic waveform data and the ECG data.

10. The apparatus of claim 9, wherein the memory further holds instructions that when executed by the at least one processor cause the apparatus to encode the LVEDP as digital data for at least one of storage, transmission, or human-comprehensible output.

11. The apparatus of claim 9, wherein the memory further holds instructions that when executed by the at least one processor cause the apparatus to determine at least one of a pre-ejection period (PEP) or an isovolumic contraction time (ICT), based on simultaneous portions of the hemodynamic waveform data and the ECG data.

12. The apparatus of claim 11, wherein the memory further holds instructions that when executed by the at least one processor cause the apparatus to calculate a contractility feature based on the hemodynamic waveform data.

13. The apparatus of claim 12, wherein the memory further holds instructions that when executed by the at least one processor cause the apparatus to calculate the LVEDP as a function of the contractility feature, at least one of the PEP and the ICT, and optionally a cuff blood pressure (DBP).

14. The apparatus of claim 13, wherein the memory further holds instructions that when executed by the at least one processor cause the apparatus to calculate the contractility feature by determining at least one of a derivative of the hemodynamic waveform data or intrinsic frequencies.

15. A method for approximation of left ventricular end diastolic pressure (LVEDP) using data from non-invasive ECG and pressure sensors coupled to a computing apparatus, the method comprising:

receiving, by at least one processor of the computing apparatus, hemodynamic waveform data from a non-invasive pressure sensor coupled to a patient and electrocardiogram (ECG) data from a non-invasive ECG sensor coupled to the patient;

determining, by the at least one processor, a time difference indicative of a delay between the hemodynamic waveform data and the ECG data; and calculating, by the at least one processor, an LVEDP based on time features and waveform features of the hemodynamic waveform data and the ECG data and the time difference, the time difference being used to determine synchronized portions in time of the hemodynamic waveform data and the ECG data.

16. The method of claim 15, further comprising encoding the LVEDP as digital data for at least one of storage, transmission, or human-comprehensible output.

17. The method of claim 15, further comprising determining, by the at least one processor, at least one of a pre-ejection period (PEP) or an isovolumic contraction time (ICT), based on simultaneous portions of the hemodynamic waveform data and the ECG data.

18. The method of claim 17, further comprising calculating, by the at least one processor, a contractility feature based on the hemodynamic waveform data.

19. The method of claim 18, wherein calculating the LVEDP further comprises calculating the LVEDP as a function of the contractility feature, at least one of the PEP and the ICT, and optionally a cuff blood pressure (DBP).

20. The method of claim 18, wherein calculating the contractility feature comprises determining at least one of a derivative of the hemodynamic waveform data or intrinsic frequencies.

21. The method of claim 15, wherein calculating the time features and waveform features of the hemodynamic waveform data and the ECG data is based on at least one of: carotid pressure waveform, aortic wall waveform, carotid vessel wall waveform, radial pressure waveform, radial vessel wall waveform, brachial pressure waveform, brachial vessel wall waveform, femoral pressure waveform, femoral vessel wall waveform, or pulseOx waveform.

22. The method of claim 15, wherein calculating the time features and waveform features of the hemodynamic waveform data and the ECG data is based on or supplemented with at least one of a flow or velocity waveform.

23. An apparatus configured to approximate left ventricular end diastolic pressure (LVEDP) using data from non-invasive ECG and pressure sensors, comprising: at least one processor coupled to a memory, to a non-invasive hemodynamic waveform pressure sensor, and to a non-invasive electrocardiogram (ECG) sensor, wherein the memory holds program instructions that when executed by the at least one processor cause the apparatus to:

receive hemodynamic waveform data from the non-invasive hemodynamic waveform pressure sensor and ECG data from the non-invasive ECG sensor;

determine a time difference indicative of a delay between the hemodynamic waveform data and the ECG data; and calculate an LVEDP based on time features and waveform features of the hemodynamic waveform data and the ECG data and the time difference, the time difference being used to determine synchronized portions in time of the hemodynamic waveform data and the ECG data.

24. The apparatus of claim 23, wherein the memory further holds instructions that when executed by the at least one processor cause the apparatus to encode the LVEDP as digital data for at least one of storage, transmission, or human-comprehensible output.

25. The apparatus of claim 23, wherein the memory further holds instructions that when executed by the at least one processor cause the apparatus to determine at least one of a pre-ejection period (PEP) or an isovolumic contraction time (ICT), based on simultaneous portions of the hemodynamic waveform data and the ECG data.

26. The apparatus of claim 25, wherein the memory further holds instructions that when executed by the at least one processor cause the apparatus to calculate a contractility feature based on the hemodynamic waveform data.

27. The apparatus of claim 26, wherein the memory further holds instructions that when executed by the at least one processor cause the apparatus to calculate the LVEDP as a function of the contractility feature, at least one of the PEP and the ICT, and optionally a cuff blood pressure (DBP).

28. The apparatus of claim 27, wherein the memory further holds instructions that when executed by the at least one processor cause the apparatus to calculate the contractility feature by determining at least one of a derivative of the hemodynamic waveform data or intrinsic frequencies.

\* \* \* \* \*